(12) United States Patent
Viola et al.

(10) Patent No.: US 9,031,701 B2
(45) Date of Patent: May 12, 2015

(54) CHARACTERIZATION OF BLOOD HEMOSTASIS AND OXYGEN TRANSPORT PARAMETERS

(75) Inventors: Francesco Viola, Charlottesville, VA (US); William F. Walker, Charlottesville, VA (US)

(73) Assignee: HemoSonics LLC, Charlottesville, VA (US)

( * ) Notice: Subject to any disclaimer, the term of this patent is extended or adjusted under 35 U.S.C. 154(b) by 220 days.

(21) Appl. No.: 13/397,481

(22) Filed: Feb. 15, 2012

(65) Prior Publication Data

US 2012/0232803 A1 Sep. 13, 2012

Related U.S. Application Data

(60) Provisional application No. 61/443,084, filed on Feb. 15, 2011.

(51) Int. Cl.
*C12Q 1/68* (2006.01)
*G01N 15/06* (2006.01)
(Continued)

(52) U.S. Cl.
CPC .............. *G01N 33/49* (2013.01); *G01N 29/024* (2013.01); *G01N 29/028* (2013.01); *G01N 2291/02466* (2013.01); *G01N 2291/02818* (2013.01)

(58) Field of Classification Search
CPC .. A61B 5/0048; A61B 5/02028; A61B 8/485; A61B 2562/028; A61B 8/00; A61B 8/06; A61B 8/0833; G01N 2291/02466; G01N 2291/02827; G01N 2291/044; G01N 29/343; G01N 29/11; G01N 29/028; G01N 29/032; G01S 15/8979; G01S 15/8995

USPC .......... 702/19; 700/266; 422/62, 68.1, 73, 80; 435/13
See application file for complete search history.

(56) References Cited

U.S. PATENT DOCUMENTS 4,112,740 A 9/1978 Brandestini
4,558,589 A 12/1985 Hemmes et al.
(Continued)

FOREIGN PATENT DOCUMENTS

WO WO2011035162 3/2011
WO 2013/055883 4/2013

OTHER PUBLICATIONS

Huang et al. Detection of Blood Coagulation and Clot Formation Using Quantitative Ultrasonic Parameters, Ultrasound in Med. & Biol., vol. 31, No. 11, pp. 1567-1573, 2005.*
(Continued)

*Primary Examiner* — Dean Kwak
(74) *Attorney, Agent, or Firm* — Meunier Carlin & Curfmann LLC

(57) ABSTRACT

An integrated system for determining a hemostasis and oxygen transport parameter of a blood sample, such as blood, is disclosed. The system includes a measurement system, such as an ultrasonic sensor, configured to determine data characterizing the blood sample. For example, the data could be displacement of the blood sample in response to ultrasonic pulses. An integrated aspect of the system may be a common sensor, sample portion or data for fast and efficient determination of both parameters. The parameters can also be used to correct or improve measured parameters. For example, physiological adjustments may be applied to the hemostatic parameters using a HCT measurement. Also, physical adjustments may be applied, such as through calibration using a speed or attenuation of the sound pulse through or by the blood sample. These parameters may be displayed on a GUI to guide treatment.

16 Claims, 20 Drawing Sheets

(51) Int. Cl.

| | | |
|---|---|---|
| G01N 21/00 | (2006.01) | |
| G01N 33/00 | (2006.01) | |
| G01N 31/12 | (2006.01) | |
| C12Q 1/56 | (2006.01) | |
| G05B 21/00 | (2006.01) | |
| G01N 33/48 | (2006.01) | |
| G01N 33/49 | (2006.01) | |
| G01N 29/024 | (2006.01) | |
| G01N 29/028 | (2006.01) | |

(56) References Cited

U.S. PATENT DOCUMENTS

| | | |
|---|---|---|
| 4,695,956 A | 9/1987 | Leveen et al. |
| 4,705,756 A | 11/1987 | Spillert et al. |
| 4,814,247 A | 3/1989 | Spillert et al. |
| 4,852,577 A | 8/1989 | Smith et al. |
| 4,900,679 A | 2/1990 | Spillert et al. |
| 5,056,357 A | 10/1991 | Dymling et al. |
| 5,104,975 A | 4/1992 | McCormick et al. |
| 5,205,159 A | 4/1993 | Carr, Jr. |
| 5,234,839 A | 8/1993 | McCormick et al. |
| 5,273,517 A | 12/1993 | Barone et al. |
| 5,311,908 A | 5/1994 | Barone et al. |
| 5,331,964 A | 7/1994 | Trahey et al. |
| 5,473,536 A | 12/1995 | Wimmer |
| 5,487,387 A | 1/1996 | Trahey et al. |
| RE35,171 E | 3/1996 | McCormick et al. |
| 5,605,154 A | 2/1997 | Ries et al. |
| 5,606,971 A | 3/1997 | Sarvazyan et al. |
| 5,655,535 A | 8/1997 | Friemel et al. |
| 5,657,760 A | 8/1997 | Ying et al. |
| 5,673,699 A | 10/1997 | Trahey et al. |
| 5,744,898 A | 4/1998 | Smith et al. |
| 5,810,731 A | 9/1998 | Sarvazyan et al. |
| 5,854,423 A | 12/1998 | Venegas |
| 5,899,861 A | 5/1999 | Friemel et al. |
| 5,921,928 A | 7/1999 | Greenleaf et al. |
| 6,039,691 A | 3/2000 | Walker et al. |
| 6,083,159 A | 7/2000 | Driscoll, Jr. et al. |
| 6,114,135 A | 9/2000 | Goldstein |
| 6,117,081 A | 9/2000 | Jago et al. |
| 6,213,950 B1 | 4/2001 | Cespedes et al. |
| 6,225,126 B1 | 5/2001 | Cohen et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,371,912 B1 | 4/2002 | Nightinggale et al. |
| 6,402,704 B1 | 6/2002 | McMorrow |
| 6,454,714 B1 | 9/2002 | Ng et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen et al. |
| 6,573,104 B2 | 6/2003 | Carr, Jr. et al. |
| 6,613,573 B1 | 9/2003 | Cohen |
| 6,632,678 B2 | 10/2003 | Aiken et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,716,168 B2 | 4/2004 | Nock et al. |
| 6,726,629 B1 | 4/2004 | Frinking et al. |
| 6,764,448 B2 | 7/2004 | Trahey et al. |
| 6,787,363 B2 | 9/2004 | Cohen et al. |
| 6,797,519 B2 | 9/2004 | Cohen et al. |
| 6,890,299 B2 | 5/2005 | Cohen et al. |
| 6,951,544 B2 | 10/2005 | Trahey et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,207,939 B2 | 4/2007 | Husher |
| 7,261,861 B2 | 8/2007 | Kautzky |
| 7,374,538 B2 | 5/2008 | Nightingale et al. |
| 7,399,637 B2 | 7/2008 | Wright et al. |
| 7,422,905 B2 | 9/2008 | Clague et al. |
| 7,439,069 B2 | 10/2008 | Nippoldt et al. |
| 7,524,670 B2 | 4/2009 | Cohen et al. |
| 7,732,213 B2 | 6/2010 | Cohen et al. |
| 7,912,661 B2 | 3/2011 | Zeng |
| 7,972,271 B2 | 7/2011 | Johnson et al. |
| 8,058,023 B2 | 11/2011 | Gurbel |
| 2002/0013530 A1 | 1/2002 | Cespedes et al. |
| 2002/0040187 A1 | 4/2002 | Alam et al. |
| 2003/0013958 A1 | 1/2003 | Govari et al. |
| 2003/0073244 A1 | 4/2003 | Cohen et al. |
| 2003/0105398 A1 | 6/2003 | Vitek |
| 2003/0171676 A1 | 9/2003 | Trahey et al. |
| 2003/0204141 A1 | 10/2003 | Nock et al. |
| 2004/0068184 A1 | 4/2004 | Trahey et al. |
| 2004/0167403 A1 | 8/2004 | Nightingale et al. |
| 2005/0004463 A1 | 1/2005 | Chen et al. |
| 2005/0015001 A1 | 1/2005 | Lec et al. |
| 2005/0053305 A1 | 3/2005 | Li et al. |
| 2005/0148899 A1 | 7/2005 | Walker et al. |
| 2007/0038095 A1 | 2/2007 | Greenleaf et al. |
| 2007/0059840 A1 | 3/2007 | Cohen et al. |
| 2007/0184508 A1 | 8/2007 | Cohen et al. |
| 2007/0276236 A1 | 11/2007 | Jong |
| 2008/0038828 A1 | 2/2008 | Cohen et al. |
| 2008/0249408 A1 | 10/2008 | Palmeri et al. |
| 2008/0261261 A1 | 10/2008 | Grimes et al. |
| 2009/0112483 A1 | 4/2009 | Cohen |
| 2011/0151491 A1 | 6/2011 | Dennis et al. |
| 2011/0252352 A1 | 10/2011 | Viola et al. |
| 2012/0252127 A1 | 10/2012 | Bansil et al. |

OTHER PUBLICATIONS

Voleisis et al. Ultrasonic method for the whole blood coagulation analysis, Ultrasonics, vol. 40, May 2002, pp. 101-107.*

Amukele, et al., "Comparison of plasma with whole blood prothrombin time and fibrinogen on the same instrument," American Journal of Clinical Pathology, vol. 133, No. 4, Apr. 2010, pp. 550-556.

Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.

Anderson, "Preventing Deep Vein Thrombosis and Pulmonary Embolism," Center for Outcomes Research, U Mass Med Center, 1998, 23 pages.

Becker, R., "Cell-based models of coagulation: a paradigm in evolution," Journal of Thrombosis and Thrombolysis, vol. 20, No. 1, Aug. 2005, pp. 65-68.

Bercoff et al., "In vivo breast tumor detection using transient elastography," Ultrasound in Medicine & Biology, vol. 29, No. 10, 2003, pp. 1387-1396.

Bercoff, et al., "Supersonic Shear Imaging: A New Technique for Soft Tissue Elasticity Mapping," IEEE Transactions on Ultrasonics Ferroelectrics & Frequency Control, vol. 51, No. 4, 2004, pp. 396-409.

Bilgen, et al., "Error analysis in acoustic elastography. II. Strain estimation and SNR analysis", Journal of the Acoustical Society of America, vol. 101, 1997, pp. 1147-1154.

Bohs, et al., "A Real Time System for Quantifying and Displaying Two-Dimensional Velocities using Ultrasound," Ultrasound in Medicine & Biology, vol. 19, No. 9, Jul. 1993, pp. 751-761.

Bonnefous, et al., "Time Domain Formulation of Pulse-Doppler Ultrasound and Blood Velocity Estimation by Cross Correlation," Ultrasonic Imaging 8, 1986, pp. 73-85.

Brock, et al., "Assessing Thrombin Generation at the Point of Care," Clinical Chemistry, vol. 55, No. 3, Mar. 2009, pp. 398-399.

Carr, M., "In vitro assessment of platelet function," Transfusion of Medicine Reviews, vol. 11, No. 2, Apr. 1997, pp. 106-115.

Carroll, et al., "Measurement of functional fibrinogen levels using the Thrombelastograph," Journal of Clinical Anesthesia, vol. 20, No. 3, May 2008, pp. 186-190.

Carter, G., "Coherence and time delay estimation," Proc IEEE, vol. 75, No. 2, 1987, pp. 236-255.

Chakroun et al., "The influence of fibrin polymerization and platelet-mediated contractile forces on citrated whole blood

(56) References Cited

OTHER PUBLICATIONS thromboelastography profile," Thrombosis and Haemostasis, vol. 95, No. 5, May 2006, pp. 822-828.
Chandler, et al., "Development of a rapid emergency hemorrhage panel," Tranfusion, vol. 50, No. 12, Dec. 2010, pp. 2547-2552.
Chandler, et al., "Estimating the rate of thrombin and fibrin generation in vivo during cardiopulmonary bypass," Blood, vol. 101, No. 11, Jun. 2003, pp. 4355-4362.
Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.
Cohn et al., "An elasticity microscope. Part I: Methods," IEEE Transactions on Ultrasonics Ferroelectrics & Frequency Control, vol. 44, 1997, pp. 1304-1319.
Cohn et al., "An elasticity microscope. Part II: Experimental Results," IEEE Transactions on Ultrasonics Ferroelectrics & Frequency Control, vol. 44, 1997, pp. 1320-1331.
Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.
Dahlback, B., "Blood Coagulation," Lancet, vol. 355, No. 9215, May 2000, pp. 1627-1632.
Emelianov et al., "Ultrasound Elasticity Imaging of Deep Venous Thrombosis," Proc. IEEE Ultrasonics Symp., 2000, pp. 1791-1794.
Evans, et al., "Rheometry and associated techniques for blood coagulation studies," Medical Engineering and Physics, vol. 30, No. 6, Jul. 2008, pp. 671-679.
Fatemi et al., "C-Scan Imaging by Radiation Force Stimulated Acoustic Emission Method," Proc. IEEE Ultrasonics Symp., 1996, pp. 1459-1462.
Fatemi, et al., "Application of radiation force in noncontact measurement of the elastic parameters," Ultrasonic Imaging, vol. 21, No. 2, Apr. 1999 pp. 147-154.
Fatemi, et al., "Ultrasound-Stimulated Vibro-Acoustic Spectography," Science Magazine, vol. 280, No. 5360, 1998, pp. 82-85.
Fertner, et al., "Comparison of Various Time Delay Estimation Methods by Comptuer Simulation," IEEE Transactions on Acoustics, Speech, and Signal Processing, vol. 34, No. 5, 1986, pp. 1329-1330.
Flax, et al., "Phase-Aberration Correction Using Signals From Point Reflectors and Diffuse Scatterers: Basic Principles," IEEE Transactions on Ultrasonics Ferroelectrics & Frequency Control, vol. 35, No. 6, Nov. 1988, pp. 758-767.
Gallippi, et al., "Adaptive clutter filtering via blind source," Ultrasonic Imaging, vol. 24, No. 4, 2002, pp. 193-214.
Gallippi, et al., "BSS-based filtering of physiological and ARFI-induced tissue and blood motion," Ultrasound in Medicine and Biology, vol. 29, No. 11, 2003, pp. 1583-1592.
Gallippi, et al., "Complex blind source separation for acoustic radiation force impulse imaging in the peripheral vasculature, in vivo," IEEE Ultrasonics Symposium, vol. 1, 2004, pp. 596-601.
Gauss, et al., "Wavefront Estimation in the Human Breast," presented at SPIE Medical Imaging, vol. 4325, 2001, pp. 172-180.
Giunta, et al., "Estimation of Global Motion Parameters by Complex Linear Regression," IEEE Transactions on Image Processing, vol. 8, No. 11, 1999, pp. 1652-1657.
Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.
Hartley, et al., "Doppler Measurement of Acoustic Streaming," IEEE Ultrasonics Symposium Proceedings, 1995, pp. 1537-1540.
Huang, et al., "Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.
Huang, et al., "Detection of blood coagulation and clot formation using quantitative ultrasonic parameters," Ultrasound in Medicine and Biology, vol. 31, No. 11, Nov. 2005, pp. 1567-1573.
Jacovitti, et al., "Discrete Time Techniques for Time Delay Estimation," IEEE Transactions on Signal Processing, vol. 41, No. 2, Feb. 1993, pp. 525-533.
Jensen, "A New Method for Estimation of Velocity Vectors," IEEE Transactions on Ultrasonics, Ferroelectrics and Frequency Control, vol. 45, No. 3, 1998, pp. 837-851.
Jensen, Estimation of Blood Velocities Using Ultrasound, 1996, pp. 195-225.
Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.
Jolliffe, IT., "Principal Component Analysis," Springer Series in Statistics, 2nd edition, Springer, NY, 2002, pp. 1-8.
Kadi, et al., "On the performance of regression and step-initialized IIR Clutter Filters," IEEE Transactions on Ultrasonics, Ferroelectrics, and Frequency Control, vol. 42, 1995, pp. 827-837.
Kasai, et al., "Real-time Two-Dimensional Blood Flow Imaging Using an Autocorrelation Technique," IEEE Ultrasonics Symposium, vol. 32, No. 3, 1985, pp. 458-464.
Kruse, et al., "A new high resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.
Ledoux, et al., "Reduction of the clutter component in Doppler ultrasound signals based on singular value decomposition: a simulation study," vol. 19, No. 1, 1997, pp. 1-18.
Lerner, et al., "Sono-elasticity: medical elasticity images derived from ultrasound signals in mechanically vibrated targets," Ultrasound in Medicine & Biology, vol. 16, 1998, pp. 317-327.
Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.
McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.
Nielson, er al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.
Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.
O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.
Ophir, et al., "Elastography: A Quantitative Method for Imaging the Elasticity of Biological Tissues," Ultrasonic Imaging, vol. 13, No. 2, 1991, pp. 111-134.
Patil, et al., "3D prostate elastography: algorithm, simulations and experiments," Physics in Medicine & Biology, vol. 52, No. 12, 2007, pp. 3643-3663.
Perry, et al., "Point-of-care testing in haemostasis," British Journal of Haematology, vol. 150, No. 5, Sep. 2010, pp. 501-514.
Libgot, R., et al., "High frequency ultrasound characterization of the blood clotting process: intra- and -inter individual variations," 2005 IEEE Ultrasonics Symposium, IEEE, vol. 4, 2005, pp. 2259-2262.
Schmitt, Cedric, et al., "Characterization of blood clot viscoelasticity by dynamic ultrasound elastography and modeling of the rheological behavior," Journal of Biomechanics, Epub., vol. 44, No. 4, 2010, pp. 622-629.
Viola, Francesco, et al., "A Novel ultrasound-based method to evaluate hemostatic function of whole blood," Clinica Chimica Acta, vol. 411, Nos. 1-2, Jan. 2010, pp. 106-113.
International Report on Patentability and Written Opinion, dated Aug. 27, 2013, in connection with corresponding International Application No. PCT/US2012/025278.
International Search Report, dated Aug. 20, 2013, in connection with corresponding International Application No. PCT/US2012/025278.
US 6,135,954, 10/2000, Cohen et al. (withdrawn).

(56) References Cited

OTHER PUBLICATIONS

Beer: Center for Reproductive Immunology & Genetics, "Thrombophilia: Inherited and Acquired," 6 pages, http://repro-med.net/papers/thromb.php.

Bell, et al., "Thrombelastographic evaluation of coagulation in transurethral prostatectomy," British Journal of Urology, vol. 78, No. 5, 1996, pp. 737-741.

Bombeli, et al., "Updates in perioperative coagulation: physiology and management of thromboembolism and haemorrhage," British Journal of Anaesthesia; vol. 93, No. 2, Aug. 2004, pp. 275-287.

Chavez, J., "A novel thrombelastograph tissue factor/kaolin assay of activated clotting times for monitoring heparin anticoagulation during cardiopulmonary bypass," Anesthesia and Analgesia; vol. 99, No. 5 Nov. 2004, pp. 1290-1294.

Curry, et al., "Convention and near-patient tests of coagulation," British Journal of Anaesthesia, vol. 7, No. 2, Apr. 2007, pp. 45-50.

Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.

Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.

Ferraris, et al., "2011 Update to The Society of Thoracic Surgeons and the Society of Cardiovascular Anesthesiologists Blood Conservation Clinical Practice Guidelines," Annals of Thoracic Surgery, vol. 91, 2011, pp. 944-982.

Freedman, et al., "A Meta-Analysis of Thromboembolic Prophylaxis Following Elective Total Hip Arthroplasty," Journal of Bone and Joint Surgery, vol. 82-A, 2000, pp. 929-938.

Gaetano, G. de, et al., "Effect of Platelets on Clot Structuration, a Thrombelastographic Study," Thrombosis Research, vol. 3, No. 4, pp. 425-435, 1973.

Ganter, et al., "Active, personalized, and balanced coagulation management saves lives in patients with massive bleeding," Anesthesiology, vol. 133, No. 5, Nov. 2010, pp. 1016-1018.

Ganter, et al., "Coagulation monitoring: current techniques and clinical use of viscoelastic point-of-care coagulation devices," Anesthesia and Analgesia, vol. 106, No. 5, May 2008, pp. 1366-1375.

Gauss, et al., "Adaptive Imagining in the Thyroid Using Fundamental and Harmonic Echo Data," presented at IEEE Ultrasonics Symposium, 1999, pp. 1515-1519.

Glidden, Paul F., et al., "Thromboelastograph Assay for Measuring the Mechanical Strength of Fibrin Sealant Clots," Clinical and Applied Thombosis/Hemostasis, vol. 6, No. 4, Oct. 2000, pp. 226-233.

Gottumukkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.

Greilich, Philip E., et al., "A Modified Thromboelastographic Method for Monitoring c7E3 Fab in Heparinized Patients," Anesth Analg, vol. 84, 1997, pp. 31-38.

Greilich, Philip E., et al., "Near-Site Monitoring of the Antiplatelet Drug Abciximad Using the Hemodyne Analyzer and Modified Thrombelastograph," Journal of Cardiothoracic and Vascular Anesthesis, vol. 13, No. 1, Feb. 1999, pp. 58-64.

Gurbel, et al., "Platelet function monitoring in patients with coronary artery disease," Journal of the American College of Cardiology, vol. 50, No. 19, Nov. 2007, pp. 1822-1834.

Harris, et al., "Evaluation of recurrent thrombosis and hypercoagulability," American Family Physician, vol. 56, No. 6, Oct. 1997, pp. 1591-1596, pp. 1601-1602.

Hett, et al., "Sonoclot Analysis," British Journal of Anaesthesia, vol. 75, No. 6, Dec. 1995, pp. 771-776.

Hirsh, et al., "How we diagnose and treat deep vein thrombosis," Blood, vol. 99, 2002, pp. 3102-3110.

Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.

Hoffman, et al., "A cell-based model of hemostasis," Thrombosis and Haemostasis, vol. 85, No. 6, Jun. 2001, pp. 958-965.

Ickx, Brigitte, "Point-of-Care Monitoring of Haemostasis in the OR and the ICU," European Society of Anaesthesiologists. Jun. 5, 2004, pp. 79-83.

International Search Report and Written Opinion of the International Searching Authority, received in corresponding application PCT/US2010/049342, Nov. 16, 2010.

International Search Report and Written Opinion of the International Searching Authority, received in corresponding application PCT/US2011/031832, Dec. 15, 2011.

Ivandic, et al., "Determination of clopidogrel resistance by whole blood platelet aggregometry and inhibitors of the P2Y12 receptor," Clinical Chemistry, vol. 52, No. 3, Mar. 2006, pp. 383-388.

Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.

Keresztes, et al., "The PFA-100: analysis and interpretation of a platelet function measurement," The Journal of Cardiovascular Nursing, vol. 20, No. 6, 2005, pp. 405-407.

Kettner, S.C., et al., "Use of abciximab-Modified Thrombelatography in Patients Undergoing Cardiac Surgery," Anesth Analg, vol. 89, 1999, pp. 580-584.

Khurana, Sandeep, et al., "Monitoring Platelet Glycoprotein IIb/IIa-fibrin Interaction with Tissue Factor-Activated Thromboelastography," J Lab Clin Med, vol. 130, No. 4, 1997, pp. 401-411.

Khurana, Sandeep, et al., "Thromboelastography Can Rapidly Bioassay Fibrinogen," Anesthesiology, vol. 85, No. 3A, Sep. 1996, p. A457.

Koepke, J., "Point-of-Care Coagulation Testing," Laboratory Medicine, vol. 31, No. 6, Jun. 2000, pp. 343-346.

Lubinski, et al., "Adaptive strain estimation using retrospective processing medical US elasticity imaging," IEEE Transactions on Ultrasonics Ferroelectrics & Frequency Control, vol. 46, 1999, pp. 97-107.

Mahla, et al., "Thromboelastography for monitoring prolonged hypercoagulability after major abdominal surgery," Anesthesia and Analgesia, vol. 92, No. 3, Mar. 2001, pp. 572-577.

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.

Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.

Nightingale, et al., "Acoustic Radiation Force Impulse Imaging: In Vivo Demonstration of Clinical Feasibility," Ultrasound in Medicine & Biology, vol. 28, 2002, pp. 227-235.

Nightingale, et al., "Acoustic remote palpation: initial in vivo results," presented at IEEE Ultrasonics Symposium, 2000, pp. 1553-1558.

Oberhardt, et al., "Dry reagent technology for rapid, convenient measurements of blood coagulation and fibrinolysis," Clinical Chemistry, vol. 37, No. 4, Apr. 1991, pp. 520-526.

O'Donnell, et al., "Role of the Thrombelastograph as an adjunctive test in thrombophilia screening," Blood Coagulation and Fibrinolysis, vol. 15, No. 3, Apr. 2004, pp. 207-211.

Packham, M., "Role of platelets in thrombosis and hemostasis," Canadian Journal of Physiology and Pharmacology, vol. 72, No. 3, Mar. 1994, pp. 278-284.

Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.

(56) References Cited

OTHER PUBLICATIONS

Parsons, et al., "Age Determiniation of Experimental Venous Thrombi by Ultrasonic Tissue Characterization," Journal of Vascular Surgery, vol. 17, 1993, 470-478.
Pivalizza, et al., "Perioperative thromboelastography and sonoclot analysis in morbidly obese patients," Canadian Journal of Anaesthesia, vol. 44, No. 9, Sep. 1997, pp. 942-945.
Rao, G., "Need for a point-of-care assay for monitoring antiplatelet and antithrombotic therapies," Stroke, vol. 40, No. 6, Jun. 2009, pp. 2271-2272.
Riou, et al., "Fast adaptive eigenvalue decomposition: a maximum likelihood approach," IEEE International Conference on Acoustics, Speech, and Signal Processing, vol. 5, 1997, pp. 3565-3568.
Rubin, et al., "Clinical application of sonographic elasticity imaging for aging of deep venous thrombosis: preliminary findings," Journal of Ultrasound in Medicine, vol. 22, 2003, pp. 443-448.
Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.
Srinivasan, et al., "Elastographic imaging using staggered strain estimates," Ultrasonic Imaging, vol. 24, 2002, pp. 229-245.
Strobach, P., "Low-rank adaptive filters," IEEE Trans Signal Process, vol. 44, No. 12, 1996, pp. 2932-2947.
Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993;71:9-15.
Vig, et al., "Thromboelastography: a reliable test?," Blood Coagulation and Fibrinolysis, vol. 12, No. 7, Oct. 2001, 555-561.
Viola, et al., "A Comparison between spline-based and phase-domain time-delay estimators," IEEE Transactions on Ultrasonics, Ferroelectrics, and Frequency Control, vol. 53, No. 3, 2006, pp. 515-517.
Viola, et al., "A comparison of the performance of time-delay estimators in medical ultrasound," IEEE Transactions on Ultrasonics Ferroelectrics & Frequency Control., vol. 50, 2003, pp. 392-401.
Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker, et al., "A Fundamental Limit on the Accuracy of Speckle Signal Alignment," IEEE Ultrasonics Symposium Proceedings, vol. 3, 1994, pp. 1787-1791.
Walker, et al., "A Method of Imagining Viscoelastic Parameters with Acoustic Radiation Force," Physics in Medicine and Biology, vol. 45, No. 6, 2000, pp. 1437-1447.
Whitten, et al., "Thromboelastography: past, present, and future," Anesthesiology, vol. 92, No. 5, May 2000, pp. 1223-1225.
Sarvazyan, et al., "Shear Wave Elasticity Imaging—A New Ultrasonic Technology of Medical Diagnostics," Ultrasound in Medicine and Biology, vol. 24, 1998, pp. 1419-1436.
Shi, Quantitative Investigation of Acoustic Streaming in Blood, J. Acoust. Soc. Am. 111, Feb. 2002, pp. 1110-1121.
Shi, et al., "Color Doppler Detection of Acoustic Streaming in a Hematoma Model," Ultrasound in Medicine and Biology, vol. 27, No. 9, 2001, pp. 1255-1264.
Shi, et al., "Color Doppler imaging of acoustic streaming in blood and clot," IEEE Ultrasonics Symposium, vol. 2, 1999, pp. 1315-1318.
Shi, et al., "Experimental Investigation and Finite Element Simulation of Streaming in Blood in Cylindrical Models," IEEE Ultrasonics Symposium, vol. 2, 2000, pp. 1509-1512.
Shung, et al., "Ultrasonic characterization of blood during coagulation," Journal of Clinical Ultrasound, vol. 12, No. 3, 1984, pp. 147-153.
Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.
Sugimoto, et al., "Tissue Hardness Measurement Using the Radiation Force of Focused Ultrasound," Proc. IEEE Ultrason. Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Viola, et al., "A Spline Based Algorithm for Continuous Time Delay Estimation Using Sampled Data," IEEE Transactions on Ultrasonics Ferroelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Sonorheometry: A new Method for Assessing coagulation potential," IEEE Ultrasonics Symposium, vol. 1, 2007, pp. 1001-1004.
Viola, et al., "Sonorheometry: A Noncontact Method for the Dynamic Assessment of Thrombosis," The Annals of Biomedical Engineering, vol. 32, 2004, pp. 696-705.
Viola, et al., "Ultrasound echo decorrelation due to acoustic radiation force," IEEE Ultrasonics Symposium Proceedings, vol. 2, 2002, pp. 1903-1906.
Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Yu, et al., "Single-Ensemble-Based Eigen-Processing Methods for Color Flow Imaging," IEEE Transactions on Ultrasonics, Ferroelectrics, and Frequency Controls, vol. 55, No. 3, 2008, pp. 573-587.

* cited by examiner

US 9,031,701 B2

CHARACTERIZATION OF BLOOD HEMOSTASIS AND OXYGEN TRANSPORT PARAMETERS

CROSS REFERENCE TO RELATED APPLICATIONS

This application claims the benefit of U.S. Provisional Application Nos. 61/443,084, filed on Feb. 15, 2011, which is incorporated by reference herein in its entirety.

ACKNOWLEDGEMENT OF GOVERNMENT SUPPORT

This invention was made with government support under Grant Nos. R43-HL103030 and R44-DK085844 awarded by the National Institutes of Health. The Government has certain rights in the invention.

BACKGROUND OF THE INVENTION

The formation of a blood clot and its successive dissolution, referred to as the hemostatic process, is required to arrest blood loss from an injured vessel. This process is the result of a delicate functional balance between plasma coagulation factors, platelets, and fibrinolytic proteins. Each of these elements plays an important role in activating/deactivating the others, and the appropriate stimuli are necessary to prevent excessive blood loss without causing inappropriate thrombosis. Disruption of this balance plays a significant role in the onset of potentially fatal conditions, including myocardial infarction, stroke, deep vein thrombosis, pulmonary embolism, and hemorrhage.

The hemostatic process is initiated by the activation and subsequent adhesion of platelets to the site of injury within the vessel wall. Activated platelets recruit other platelets and interact with fibrinogen in the blood plasma to form a platelet-plug that serves as the initial response to stop blood loss. Hemostasis then proceeds with a cascade of proteolytic reactions of the plasma coagulation proteins that ultimately form a three-dimensional network of fibrin that strengthens the platelet-plug. The fibrin chains are cross-linked and stabilized by the plasma factor XIIIa (FXIIIa). Platelets also have a central role in regulating the process of fibrin polymerization. The final step of hemostasis (i.e., fibrinolysis or clot dissolution) involves the activation of the plasma protein plasmin, which lyses the blood clot when its useful life is over. This cell-based model of hemostasis closely reflects the in vivo physiological process.

SUMMARY OF THE INVENTION

The present invention overcomes the problems of the prior art by providing a system for measuring a parameter of a blood sample. The system may include, for example, an ultrasonic signal generator, a receiver and a processor. The ultrasonic signal generator is configured to generate and direct an ultrasonic signal to interact with the blood sample. The receiver is configured to determine at least one characteristic of the ultrasonic signal that interacted with the blood sample. The processor is configured to determine, using the characteristic, at least one hemostasis parameter and at least on oxygen transport parameter.

The oxygen transport parameter may include HCT, HGB, MCV, RBC, MCHC, MCH and combinations thereof. The processor may be further configured to generate a corrected hemostasis parameter using the oxygen transport parameter.

The hemostasis parameter may be a TC1, TC2, angle, and estimated stiffness S. Also, the hemostasis parameter may be an index for a clinical parameter, such as (1) coagulation factors (intrinsic and/or extrinsic), (2) platelet function, (3) fibrinogen and (4) fibrinolysis.

The processor may also be configured to communicate the clinical parameter to guide transfusion, such as through a graphical user interface (GUI). The clinical parameter may be (1) fresh frozen plasma, (2) platelet concentrates, (3) cryo-precipitate, (4) antifibrinolytics, and (5) packed RBCs.

The processor may also be configured to communicate the HCT or other oxygen transport parameter. It could also compare the HCT to an assumed HCT and communicate a difference therebetween. Or, it could determine when the HCT is within a range affecting the parameter and communicate a warning about the parameter.

In addition, a system for evaluating a blood sample could include a processor configured to determine a hemostasis parameter from the blood sample and to determine at least one oxygen transport parameter from the same blood sample. The system may also include an ultrasound generator and a receiver. The receiver is configured to receive reflected sound from the blood sample and to convert the received sound into electrical signals. The hemostasis parameter is measured by quantifying the displacement induced within the blood sample by application of at least one pulse of ultrasound of sufficient intensity to induce measurable displacement within the blood sample.

A method includes measuring at least one hemostasis parameter from the blood sample. Also, the method includes measuring at least one oxygen transport parameter from the same blood sample.

A system for determining properties of at least one tissue sample may include a measurement system, a processor and an integrated aspect. The measurement system is configured to determine date characterizing the tissue sample. The processor is configured to receive the data and to determine at least one hemostasis parameter and at least one oxygen transport parameter using the data. The integrated aspect is configured to facilitate determination of the at least one hemostasis parameter and at least one oxygen transport parameter. The data, for example, may be generated by an application of force to the tissue sample.

The integrated aspect may be a common sample portion. The common sample portion is characterized by the hemostasis parameter and oxygen transport parameter. A sample container may be included to contain the common sample portion. The common sample portion may be a blood sample, for example.

The integrated aspect may also be a receiver of the measurement system, wherein the receiver is configured to determine displacement of the tissue sample.

The integrated aspect may also include an ultrasonic signal generator of the measurement system. It may be configured to generate and direct an ultrasonic signal to the tissue sample to induce the displacement. The processor may be configured to determine a stiffness of the tissue sample using the displacement. The stiffness can be used to determine the hemostasis parameter.

The data may also include a speed of sound through the tissue sample. The processor is configured to use the speed of sound to determine the oxygen transport parameter. The data may also include attenuation of the ultrasonic signal through the tissue sample and use the attenuation to determine the oxygen transport parameter. The speed of sound and/or attenuation can also be used to calibrate the system.

The ultrasonic signal generator may be configured to adaptively adjust the ultrasonic signal. For example, it may generate a convoluted pulse and the process may be configured to process a corresponding correlation function. For example, the convoluted pulse may be convolved with a Barker code.

Also, the measurement system may operate in two phases. A first phase determines first phase data and a second phase determines second phase data. The first phase data is used to determine the hemostasis parameter. The second phase data is used to determine the oxygen transport parameter. The phases may occur in series.

Also, the measurement system may be configured to determine the data by querying a plurality of channels. And, the system may be configured to operate in a plurality of cycles. Each cycle includes acquisition of the data by the measurement system and processing of the data by the processor.

The processor may be further configured to adjust the hemostasis parameter using the oxygen transport parameter.

The integrated aspect may also include a common portion of the data used by the processor to determine the oxygen transport parameter and the hemostasis parameter.

The oxygen transport parameter may, for example, be one or more of HCT, HGB, MCV, RBC, MCHC and MCH.

The integrated aspect may also include an ultrasound transducer and receiver of the measurement system. The transducer and receiver may be positioned on opposite sides of the tissue sample.

Also, the processor may be configured to perform a physiological adjustment to the hemostasis parameter. For example, the physiological adjustment may be based on the oxygen transport parameter. Also, the processor may be configured to perform a physical adjustment to the hemostasis parameter. For example, the physical adjustment may be based on one of a speed or attenuation of a sound signal through the tissue sample.

The system may also include a GUI configured to display both the hemostasis parameter and the oxygen parameter simultaneously.

These and other features and advantages of the present invention will become more readily apparent to those skilled in the art upon consideration of the following detailed description and accompanying drawings, which describe both the preferred and alternative embodiments of the present invention.

DETAILED DESCRIPTION OF THE INVENTION

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

The present invention provides methods, apparatus and systems for performing what the present inventors have termed sonorheometry. Sonorheometry provides data about the mechanical properties of soft tissue. Furthermore, repeated measurements using sonorheometry enable characterization of changing properties over time. Sonorheometry is particularly well-suited to characterizing blood coagulation and clot dissolution (i.e., the hemostatic process). The present invention provides data about the mechanical properties of a developing and later dissolving clot without disrupting the underlying processes. The methods and techniques may be non-invasive or carried out in a laboratory setting after obtaining a sample from a patient, and are based on the application of acoustic radiation force to the tissue to be characterized.

An increased or decreased propensity to clot can be evaluated by observing the coagulation rate and mechanical characteristics of the developing clot at any time during formation and dissolution. This information may in turn allow clinicians to assess an individual's clotting behavior and to treat coagulation disorders appropriately. This information may also be used to evaluate whether a particular treatment and/or dosage is effective or needs to be changed, as subsequent testing according to the present methods (i.e., after a treatment has been administered) can be carried out to compare the results, thereby indicating the effect of the treatment.

I. Determination of Hemostasis Indexes

Figure 1A:
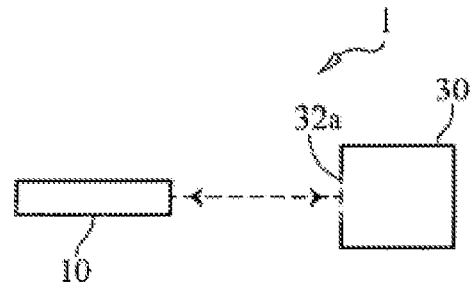
FIG. 1A is a schematic representation of the present invention useful for in vitro characterization of a soft tissue sample such as blood.

Referring now to FIG. 1A, an assembly 1 is schematically shown that is set up for testing soft tissue according to the present invention. An acoustic wave generating device 10 is positioned in alignment with container 30 to allow device 10 to irradiate a soft tissue contained within container 30. Device 10 may be mounted or fixed at a predetermined distance for the contents of the container 30 to receive focused acoustical waves from device 10. Thus, device 10 and container 30 are oriented to align the emission of acoustic waves from device 10 with a sample contained in container 30.

Figure 1B:
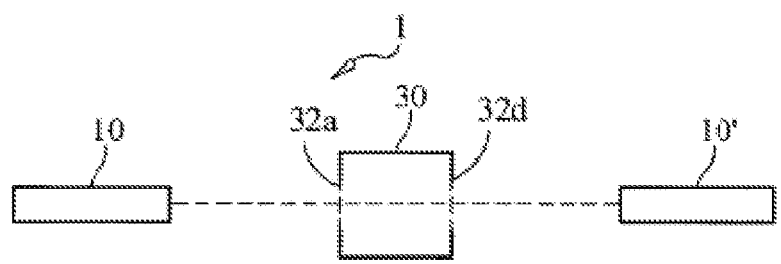
FIG. 1B is a modification of the arrangement shown in FIG. 1A in which an additional transducer is positioned on a side of the container opposite the device that is also shown in FIG. 1A.

Container 30 may be entirely acoustically transparent, or contains at least one window 32a that is acoustically transparent and that is aligned with the emission pathway of device 10. As one non-limiting example, container 30 may include a plastic cuvette having windows 32a and 32d, as shown in FIG. 1B, cut therethrough and covered with KAPTON® (polyimide) film or other at least partially acoustically permissive material.

It may be advantageous to place the acoustic window or windows of the sample container at some non-perpendicular angle relative to the direction of wave propagation so as to reduce the magnitude of received echoes from the interfaces with the window(s). Multiple measurements may be performed at the same time using an array of sample containers 30.

An array may either include multiple individual containers or a single container with multiple sample compartments. Additionally or alternatively, an array of transducers may be included in device 10, or an array of devices 10 may be used to make multiple measurements. Thus, for example, multiple transducers and/or multiple devices 10 may be provided to analyze multiple samples in parallel, wherein the multiple samples are contained in multiple individual containers or a single container with multiple sample compartments.

Assembly 1 may be submerged in a tank of water or other coupling medium to facilitate transmission of the acoustic waves. Alternatively, device 10 (or other acoustic emitter and receiver) may be placed in direct contact with the sample. Still further, device 10 may be adapted to deposit the sample directly in contact therewith, for example placing a drop (or other quantity) of blood on a transducer contained in device 10 or other application feature of device 10. In the case where a bath (of water or other coupling medium) is provided, the bath may be a constant temperature bath or other means may be provided to maintain a constant sample temperature.

In cases where no bath is used, it may be advantageous to place the sample in contact with a material of controlled temperature, so as to control the sample temperature. Another alternative is the use of device 10 invasively. For example, device 10 may be inserted intra-vascularly and delivered to the location of a stent to characterize any clotting that may be occurring as well as characterize the progression or stage of a clot that may be present.

Similar intravascular techniques can be applied for identifying and/or characterizing clot processes with regard to Deep Vein Thrombosis (DVT), as well as for other clotting events throughout the body, as long as the location is accessible by catheter or other delivery instrument, for example. Thus, not only are intravascular insertions, deliveries or locations made possible by the device, but the device may also be positioned at an intra-cavity location or other location inside of the body.

One could also apply the invention from outside the body and rather than looking at maximum displacement, look at the time constant of the displacement to characterize clot characteristics or evolution.

Device 10 includes an acoustic wave generating source capable of generating one or more pulses, at least one of which is of sufficient intensity to induce measurable physical displacement in the soft tissue contained in container 30. For example, device 10 may include one or more piezoelectric transducers capable of generating ultrasonic waves. Alternatively, device 10 may utilize an electric circuit to generate rapid heating and thereby generate acoustic energy.

Further alternatives may be employed for generating acoustic energy, including, but not limited to: an ultrasonic generator fabricated using microelectromechanical systems (MEMS); a capacitive micromachined ultrasound transducer; a laser used to heat a target material thereby generating acoustic energy, where the laser may be targeted on a permanent component of the assembly, or on a surface of the sample, for example. Still further alternatively, a transducer may be incorporated into the sample container 30 in lieu of providing it in the device 10, as in a case, for example, where a polymer transducer material such as PVDF may be glued right onto the surface of the sample container 30.

Device 10 further includes at least one sensor capable of measuring displacement or deformation induced by the acoustic waves as they are applied to the soft tissue sample and reflected by the soft tissue sample back to device 10. In this configuration, an ultrasound sensor may be used to track the motion of the sample as induced by at least one ultrasonic wave of sufficient intensity to induce displacement of the tissue.

Alternatively, tracking of the motion may be accomplished by means other than sensing reflected acoustic waves. For example, optical coherence tomography, a focused light interferometer or laser Doppler may be used to optically sense the displacement of the tissue induced by the one or more ultrasonic waves.

Device 10 may include one or more sensors for carrying out any of these optical methods or such sensors may be provided in equipment that is separate from device 10. Likewise, for acoustic sensing, the one or more sensors may be one and the same as the acoustic wave generator, or may be a separate component(s) and may take any of the forms described above with regard to the acoustic wave generating component. An ultrasonic transducer may be used to both apply ultrasonic waves to the soft tissue as well as to sense ultrasonic waves reflected back from the tissue. An adjoining processor (not shown in FIG. 1A) may be provided to control the timing of transmission of pulses and of receiving of echoes (reflected pulses) by device 10.

FIG. 1B shows an example wherein a second device 10' is positioned in alignment with device 10, but on the opposite side of container 30 compared to the location of device 10. In this example, container 30 may be entirely acoustically transparent, or contain at least two windows 32a and 32d that are acoustically transparent and that are aligned with the emission pathway of device 10 to permit emissions to pass through both windows 32a and 32d to be received by device 10'. System 1 shown in FIG. 1B, in addition to performing the measurements that the system of FIG. 1A performs, can also measure acoustic properties, including speed of sound and attenuation, which provide indirect measures of tissue microstructure and which may be used for calibration purposes.

Acoustic radiation force arises from two sources, a non-zero time-averaged sound pressure in the ultrasonic beam, and the momentum transported by the beam. The momentum transfer component of this force dominates under most conditions. This momentum transfer results from attenuation of the propagating ultrasound beam via both absorption and scattering. For the case of total absorption the applied radiation force is simply:

$$F = W/c \qquad (1)$$

where W is the acoustic power and c is the speed of sound in the medium. In the case of perfect reflection this radiation force is doubled. In both cases, radiation force acts along the direction of wave propagation.

In biological media absorption and reflection are neither total, nor isolated at interfaces. Rather, attenuation and reflection (in the form of scattering) occur throughout volumes of tissue. In these cases radiation force acts as a body force, with the force on a given volume simply equal to the sum of the force from absorption and that from scattering. If we assume that scattering in the tissue consists purely of backscatter, which is of course overly simplistic, then the radiation force applied to a given volume of tissue is:

$$F = Wa/c + 2Ws/c \qquad (2)$$

where Wa is the absorbed ultrasound power and Ws is the scattered ultrasound power within the volume. If we further simplify by recognizing that only a fraction of the scattered energy is returned as backscatter, and that attenuation is dominated by absorption rather than scattering, then (2) can be simplified as:

$$F = Wa/c = (A/c)I_0(e^{-2\alpha f z_1} - e^{-2\alpha f z_2}) \qquad (3)$$

where A is the cross sectional area of the volume of interest (perpendicular to the axis of propagation), $I_0$ is the ultrasound intensity that would be observed in the absence of attenuation, $\alpha$ is the amplitude attenuation coefficient in Nepers per centimeter per MHz, f is the ultrasonic center frequency in MHz, and $z_1$ and $z_2$ are the ranges of the front and back of the volume in units of centimeters.

By utilizing two devices 10 and 10', wherein device 10 at least contains an emitter and device 10' contains at least a sensor for receiving the waves/pulses that pass through windows 32a, 32d the system can also measure the waves that pass from device 10 to device 10' and estimate acoustic properties of the sample being analyzed. Examples of acoustic properties that may be estimated include attenuation, scattering, and speed of sound during sonorheometry procedures. The data received by device 10' may be used to make predictions/estimations of the applied radiation force and compare experimentally determined displacements to predicted displacements.

Figure 1C:
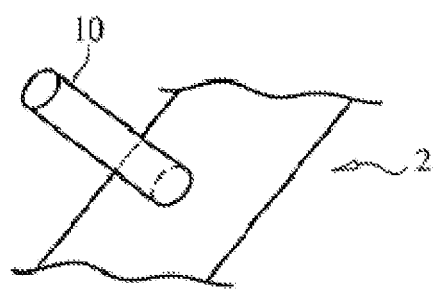
FIG. 1C schematically illustrates a non-invasive use of the present invention.

It should be noted that although FIG. 1A shows an example of apparatus for performing analysis in vitro (such as in a laboratory setting, or from a self-operated testing kit, for example) after taking a sample to be analyzed from a patient and depositing it in container 30. Alternatively, the present invention may also be practiced non-invasively, such as by applying acoustic waves from a device 10 transdermally through a patient (in vivo) to the targeted tissue to be analyzed, see FIG. 1C.

A single time frame analysis of one or more physical properties of the tissue may be made, or time series studies may be performed by applying the waves transdermally at different time periods, using the techniques described herein for the in vitro studies. Generally, the in vivo analyses would not involve administration of thrombin or other coagulant to a patient. However time studies may be done to test the effectiveness of an anti-clotting treatment regimen for example. Similarly, time studies may be done to test the effectiveness of a pro-clotting regimen given to a patient to increase the ability of the blood to clot, such as in the case of a hemophiliac, for example. Likewise, the administration of thrombin is not necessarily required for time studies in vitro, as there are other techniques that may be substituted to initiate coagulation, such as snake venom, kaolin, celite, tissue factor, the use of ground glass to initiate coagulation, etc.

Non-invasive applications of the current invention include characterizing a stage of development of a blood clot by generating a series of acoustic pulses and transdermally directing the series of pulses into the blood such that at least one of the pulses are of sufficiently high intensity to induce physical displacement of the blood, receiving at least two pulses, including at least one pulse reflected from the blood to establish a baseline and another pulse reflected from the blood to estimate at least one characteristic of the physical displacement induced by the waves.

Alternatively, the at least two pulses identified above as being used for establishing baseline and estimating a characteristic resulting from the physical displacement of the sample, do not necessarily have to be reflected from the blood/sample. For example, if the sample is contained within membranes that move with the movement of the blood/sample or in a container 30 that is sufficiently flexible (such as a membranous container, for example) to move with the movements of the blood/sample, then the at least two pulses could alternatively be those reflected from the surfaces of the flexible sample container or other membranes placed within the sample, as the movement of the sample (e.g., development of the clot) will alter the position of the surfaces or membranes.

The at least one estimate may be compared to previously generated data to gauge the stage of development of the blood clot being analyzed. The previously generated data may be reference data, such as generated across a larger number of patients and then averaged to determine normal characteristics, as well as to find average levels for characterizing different stages of clotting for example. Optionally, one or more algorithms, techniques or statistical processes may be applied to the at least one estimate to correct for attenuation, scatter and/or other variables before making comparisons to the previously generated data and/or database.

Additionally, or alternatively, the prior data or previously generated data may be data generated from one or more previous applications of the present invention to the same patient for the same tissue at prior times. This approach may be used to develop a history, to show the progression of the development of the clot for example. Of course, the in vitro apparatus described herein could be used to carry out the same tests outside of the body, such as in a laboratory or a patient's home test kit.

Still further evaluation of the effectiveness of an anti-clotting treatment may be performed, such as by evaluating the blood prior to application of the treatment by generating a series of acoustic pulses and directing the series of pulses into the blood such that at least one of the pulses is of sufficiently high intensity to induce physical displacement of the blood, receiving at least two pulses reflected from the blood to establish a baseline and to estimate at least one characteristic of the physical displacement induced by the waves, and then repeating these steps at least one time after administration of the treatment.

As noted earlier, alternative sensing or receiving steps may be taken to track the movement of the blood, such as by using any of the alternative sensing techniques described above, e.g., laser Doppler, optical coherence tomography, etc. Repeated applications of the steps at predetermined time intervals may be performed if needed to ensure a stabilization of the properties measured, as a result of the treatment. Alternatively, the analysis may indicate that a larger or smaller dose of treatment is needed, or that the treatment is ineffective for a particular patient.

Alternatively, evaluation of the effectiveness of an anti-clotting treatment may be performed by carrying out the analysis steps a number of times after treatment, at predetermined time periods after the administration of the treatment, for example. The results generated from each iteration can then be compared and analyzed to note any changes in the at least one physical characteristic that is being measured/estimated.

Maintenance monitoring can be carried out by the same techniques noted, wherein a patient can be periodically tested to ensure that a clot has not progressed further and/or is dissolving.

Figure 2:
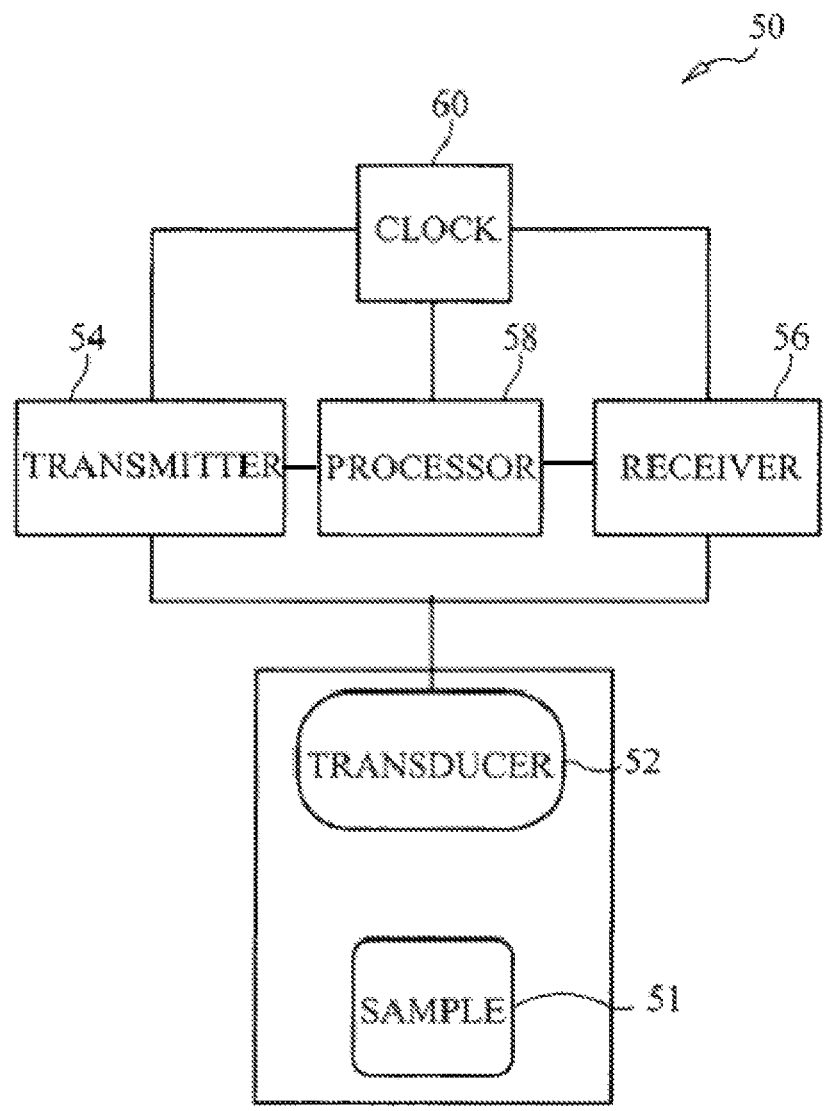
FIG. 2 is a schematic representation of a system for characterization of at least one physical property of soft tissue.

FIG. 2 shows a schematic representation of an example of a system 50 for characterization of changes in physical properties of soft tissue over time. In this example, a transducer 52, such as may be contained in a device 10 as described above, or directly mounted, fixed to or integral with a container holding a sample 51, for example, is connected to a transmitter 54 as well as receiver 56, both of which are controlled by processor 58 and timed by clock 60.

Clock 60 is provided to control the timing of application of radiation to the sample as generated by transmitter and converted to the acoustic energy at transducer 52, as well as the timing of receiving and interpreting the reflected waves (echoes), by conversion through transducer 52 and receipt of the converted signals at receiver 56, all of which is controlled by one or more processors/microprocessors 58.

Displacements of the soft tissue may be induced by delivering one or more acoustic pulses according to a predetermined frequency through device 10.

The displacements may be estimated by applying one or more signal processing algorithms (e.g., minimum sum squared difference motion tracking algorithm, etc.) to the acquired echoes of every nth delivered pulse where "n" is a predefined integer. Alternatively, the signal processing algorithms may be applied to every pulse received. Similarly, algorithms may be applied at every nth time interval for optical waves received.

Parameter measurement may be initiated at a predetermined time after one or more coagulation reagents are added to the sample, and such measurements may be repeatedly performed, e.g., once after each passage of a pre-designated time period or according to pre-defined time intervals for measurement. At each acquired time lapse, a time-displacement curve may be generated from which the viscoelastic parameters of the sample can be determined.

Figure 3:
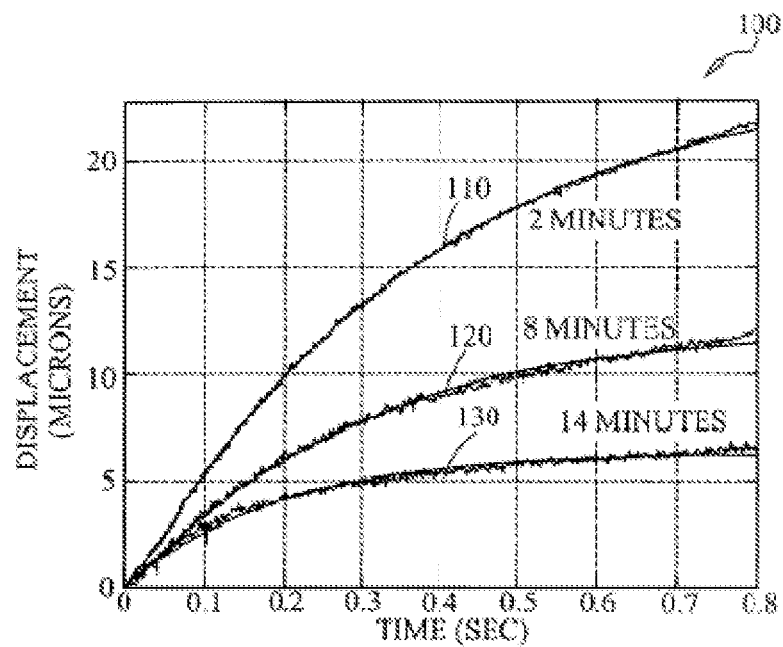
FIG. 3 shows a series of time-displacement curves comparing values found by fitting a model to values obtained using an embodiment of the present apparatus.
Figure 4:
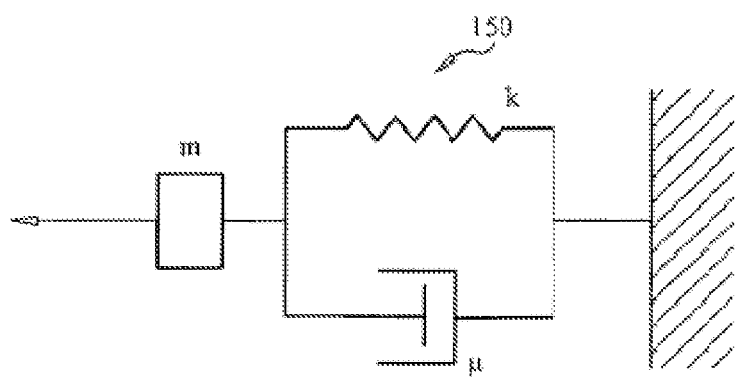
FIG. 4 is a symbolic representation of a modified Voigt model used as a model to characterize the behavior plotted in FIG. 3.

FIG. 3 is a graph 100 showing a set of time-displacement curves 110, 120, 130 obtained during coagulation of a blood sample using the techniques described. Curves 110, 120 and 130 are superimposed on accompanying model predictions, where the mechanical properties of the forming thrombus are modeled by a modified Voigt model 150 as shown in FIG. 4. Experimental results and theoretical predictions show excellent agreement. The basis of the model from which the mechanical parameters are derived is the Voigt model in series with an inertial component. It should be noted that this is not an independent model. Rather, it is a parametric fit. The model is applied to determine the parameter values that give the best fit.

The modified version 150 of the Voigt model may be used to model the viscoelastic response of blood to acoustic radiation force from which mechanical parameters of the blood may be estimated. Model 150 includes an inertial component "m" in series with the traditional Voigt model, which includes a spring k in parallel with a dashpot μ, as shown in FIG. 4. The governing differential equation for the model is:

$$F(t)=kx(t)+\mu dx(t)/dt+m\, d^2x(t)/dt^2 \quad (4)$$

where F(t) is the applied force as a function of time, x(t) is the induced displacement as a function of time, k is the elastic constant, μ is the viscous constant, and m is the inertial component.

System 50 applies radiation force by transmitting a series of pulses to the same location in the blood sample. Assuming that the pulse-to-pulse interval is much shorter than the time constant of the blood's mechanical response, the forcing function may be modeled as a temporal step function as follows:

$$F(t)=Au(t) \quad (5)$$

where A is the force amplitude. Substituting equation (5) into equation (4) and solving for the displacement yields:

$$x(t) = \frac{\zeta\sqrt{\zeta^2-1}}{2\sqrt{\zeta^2-1}} s \cdot e^{\left(-\zeta+\sqrt{\zeta^2-1}\right)\omega t} + \frac{\zeta-\sqrt{\zeta^2-1}}{2\sqrt{\zeta^2-1}} s \cdot e^{\left(-\zeta-\sqrt{\zeta^2-1}\right)\omega t} + s \quad (6)$$

where ζ is the damping ratio, ω is the natural frequency (in radians per second) and s is the static sensitivity. These parameters are defined as:

$$\zeta = \frac{\mu}{2\sqrt{k \cdot m}} \quad (7)$$

$$\omega = \sqrt{\frac{k}{m}} \quad (8)$$

$$s = \frac{A}{k} \quad (9)$$

In the examples described herein, the force scaling constant A was not measured. Thus the time-displacement data in this situation can only be used to solve for relative parameters. To address this limitation, the equations (7), (8) and (9) are redefined according to the following equations (10), (11) and (12) using relative measures of elasticity $k_r$, viscosity $\mu_r$, and mass $m_r$:

$$\zeta = \frac{\mu_r}{2\sqrt{k_r \cdot m_r}} \quad (10)$$

$$\omega = \sqrt{\frac{k_r}{m_r}} \quad (11)$$

-continued $$s = \frac{1}{k_r} \quad (12)$$

where $k_r=k/A$, $\mu_r=\mu/A$ and $m_r=m/A$.

Although the viscosity, elasticity and inertia are measured as force-dependent parameters, the natural frequency and the damping ratio still remain force-free or force-independent parameters. It is further possible to define a third force-independent parameter, i.e., the time constant τ as:

$$\tau = \frac{\mu_r}{k_r} \quad (13)$$

The fact that the actual data shown in FIG. 3 waivers or oscillates somewhat about the model data curves suggest that a different model might be used to even more closely model the behavior. In one possible modification, a dashpot would be placed in series with the model shown in FIG. 4. However, the model of FIG. 4 accurately described the response of the blood during formation of a clot with correlation between the data and the model of FIG. 3 being greater that 99% in most of the cases analyzed.

Alternatively, among the parameters obtained by the curve fitting, it is possible to use the estimated displacement magnitude at 1 second as a qualitative measure of the mechanical properties (i.e., stiffness) of the sample. When blood is in viscous fluid state, the displacement at 1 second is high. As the blood coagulates this displacement decreases relative to the generation of the fibrin mesh and activity of platelets. The value increases again during the process of fibrinolysis.

The displacement values obtained at 1 second for each data acquisition are compiled to form a curve showing relative stiffness as a function of time. This curve characterizes hemostasis and can be further processed to estimate direct indices of hemostatic function (See, e.g., FIG. 9). Other curves, using other reagents, may also be employed to facilitate estimation of, or separately determine, the hemostatic indices.

Indices of hemostasis are calculated by fitting a sigmoidal curve to the stiffness-time curve and evaluating the first derivative of the curve as described in Mauldin F W, Viola F et al. *Adaptive force sonorheometry for assessment of whole blood coagulation*. Clinical Chimica Acta 2010; 411:638-644. For example, the times to clot $TC_1$ and $TC_2$ are calculated based on a threshold value of the derivative curve (20% of the minimum value), and are indicative of the beginning and ending phase of fibrin polymerization. The clotting slope CFR is the maximum of the derivative curve and is indicative of the rate of fibrin polymerization. Additionally or alternatively to calculation of CFR as described, an angle θ can be defined as the slope of the line between $TC_1$ and $TC_2$. The stiffness S is estimated from the stiffness curve 3 minutes after $TC_2$. S depends upon platelet function and the final stiffness of the fibrin network. Identical methods and indices are calculated for the fibrinolytic process. In particular the times $TL_1$ and $TL_2$ can be defined to represent the initial and final phases of the fibrinolytic process and the consequent dissolution of the fibrin network (time to lysis).

A summary of the parameters generated for each test well is presented in the table below:

TABLE I

| Parameter | Information provided | Dependent upon |
|---|---|---|
| $TC_1$, $TC_2$ | Measure initial and final fibrin formation | Function of fibrinogen and other coagulation factors |
| S | Fibrin and platelet activity | Function of fibrin network and platelet aggregation |
| CFR, θ | Rate of fibrin polymerization | Function of fibrinogen and other coagulation factors |
| $TL_1$, $TL_2$ | Clot dissolving process | Function of fibrinolytic proteins of the plasma |

In order to isolate the four main components of hemostasis, four sonorheometry measurements are performed in parallel using a combination of agonists and antagonists reagents. In a possible embodiment, test well 1 might have kaolin powder to activate coagulation through the intrinsic pathway. Test well 2 might have a combination of kaolin and abciximab (ReoPro) to inhibit platelet aggregation. Test well 3 might have abciximab and thrombin to activate coagulation through the common pathway. Test well 4 might have tissue factor to activate coagulation through the extrinsic pathway. The measurements in each well are combined to form indices of hemostasis as shown in the table below:

TABLE II

| Output | Method |
|---|---|
| Coagulation factors Index (Intrinsic Pathway) | Time to clot $TC_1$ in well #1 |
| Coagulation factors Index (Extrinsic Pathway) | Time to clot $TC_1$ in well #4 |
| Platelets Index | Stiffness S differential between well #1 and well #2 |
| Fibrinogen Index | Stiffness S in well #3 |
| Fibrinolysis Index | Time to lysis $TL_1$ in well #4 |

EXAMPLE

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Blood samples were obtained from a peripheral vein of the arm of a patient into six 1.8 ml Vacutainers (Becton Dickinson, Franklin Lakes, N.J.) containing 3.2% (0.105M) sodium citrate to prevent coagulation within the tubes. The first tube was discarded, while the remaining tubes were placed on a rocker table and analyzed sequentially starting thirty minutes after the draw. For all the experiments described here, samples were obtained from a total of eight volunteers (four male and four female) with age range of twenty-three to thirty years (mean and standard deviation of 25.75±3.3 years) and with no history of thrombotic or hemorrhagic disorders. Ultrasound pulses having 10 Mhz center frequency were applied, pulse repetition frequency (PRF) was adaptively adjusted with the range of about 25 Hz to about 12.8 kHz. Automated measurements having a one second acquisition time were performed every six seconds.

In a typical experiment, 1 ml of citrated blood was pipetted into a 4 ml clear polystyrene cuvette along with 0.5 mg of kaolin activator to start coagulation through activation of the intrinsic pathway and 62 µl of 0.2M $CaCl_2$ to reverse the anticoagulant effect of the sodium citrate. Other reagents were also added as required by the specific study performed. Phosphate Buffer Saline (PBS) solution was added to maintain identical blood dilution. Sonorheometry data acquisition was initiated one minute after all the reagents were pipetted into the sample, and measurements were performed every six seconds.

Gly-Pro-Arg-Pro (GPRP) was obtained from Calbiochem (EMD Chemicals Inc., Gibbstown, N.J.) with 99.1% purity as determined by HPLC. GPRP was dissolved in PBS into 100 mM stock. Kaolin was obtained in powder form (Sigma Aldrich, St. Louis, Mo.) and suspended in sterile sodium chloride solution (Becton Dickinson, Franklin Lakes, N.J.). Monoclonal antibody abciximab (ReoPro, Eli Lilly and Company, Indianapolis, Ind.) was obtained in a concentration of 2 mg/ml. The original solution was diluted by a factor of five by adding 200 µL of PBS into 50 µl of the original ReoPro solution. The serine protease abbokinase (urokinase-type Plasminogen Activator, or uPA, Hyphen Biomed, Neuville-sur-Oise, France) was obtained in a concentration of 1 unit/µl.

Pulse-to-pulse time delays were estimated using a spline-based estimator as described in Viola F, Walker WF. *A Spline Based Algorithm for Continuous Time Delay Estimation Using Sampled Data*. IEEE Trans Ultrason Ferroelect Freq Cont 2005; 52:80-93 and assembled to generate time-displacement curves, similar to those depicted in FIG. 3. The value of the induced displacement at 1 second was extrapolated from each curve, and the extrapolated displacement values were then normalized by their corresponding PRF and combined to form a stiffness vs. time curve similar to that shown in FIG. 9.

Results

Assessment of Coagulation Plasma Factors and Fibrin Polymerization

Figure 10:
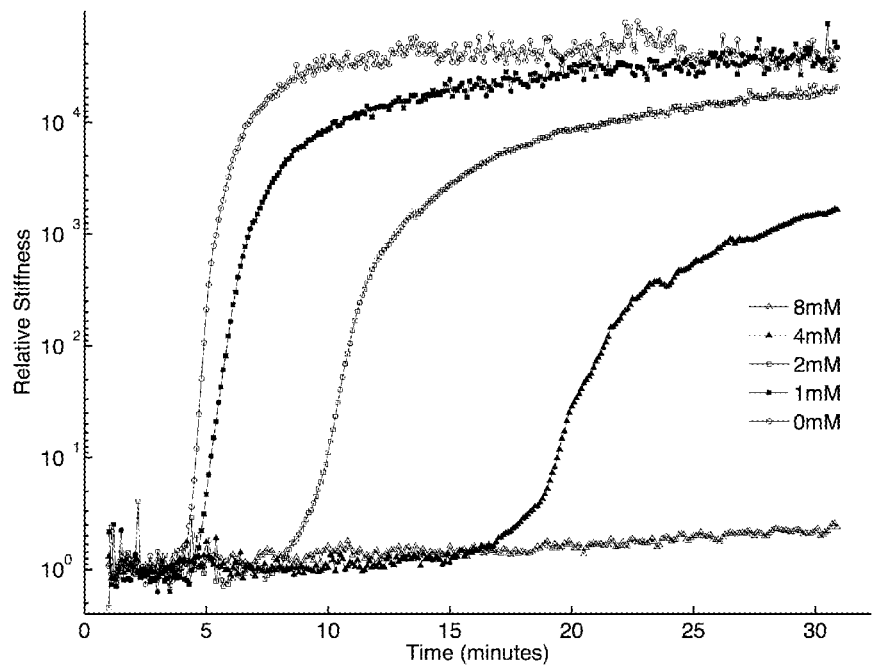
FIG. 10 is a plot of a curve showing sonoheometry measured clot stiffness at a range of GPRP concentration.
Figure 11:
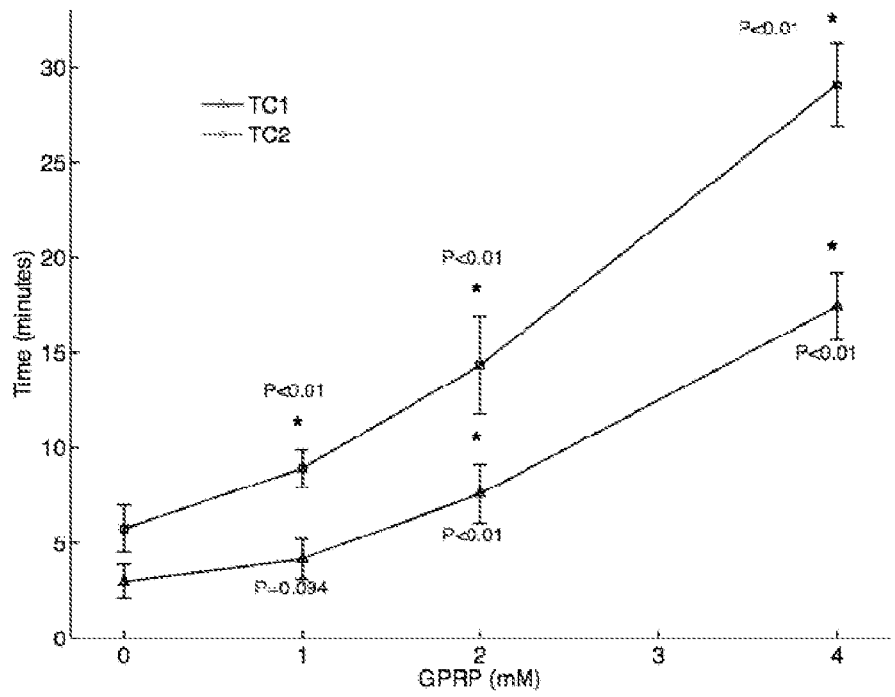
FIG. 11 is a plot of a curve showing initial (TC1) and final (TC2) clotting times increasing with concentration of GPRP.
Figure 12:
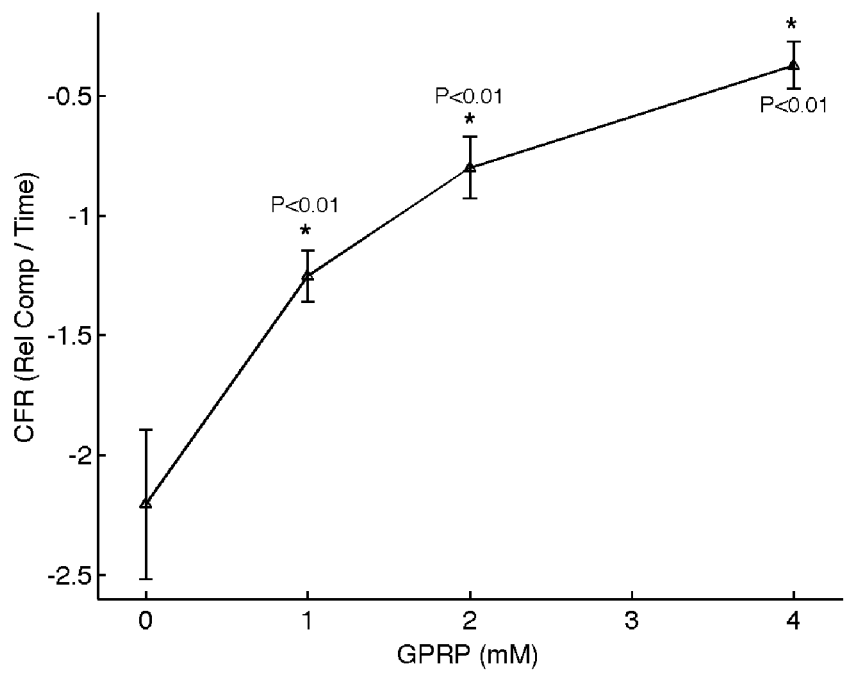
FIG. 12 is a plot of showing clot formation rate with varying GPRP concentration.
Figure 13:
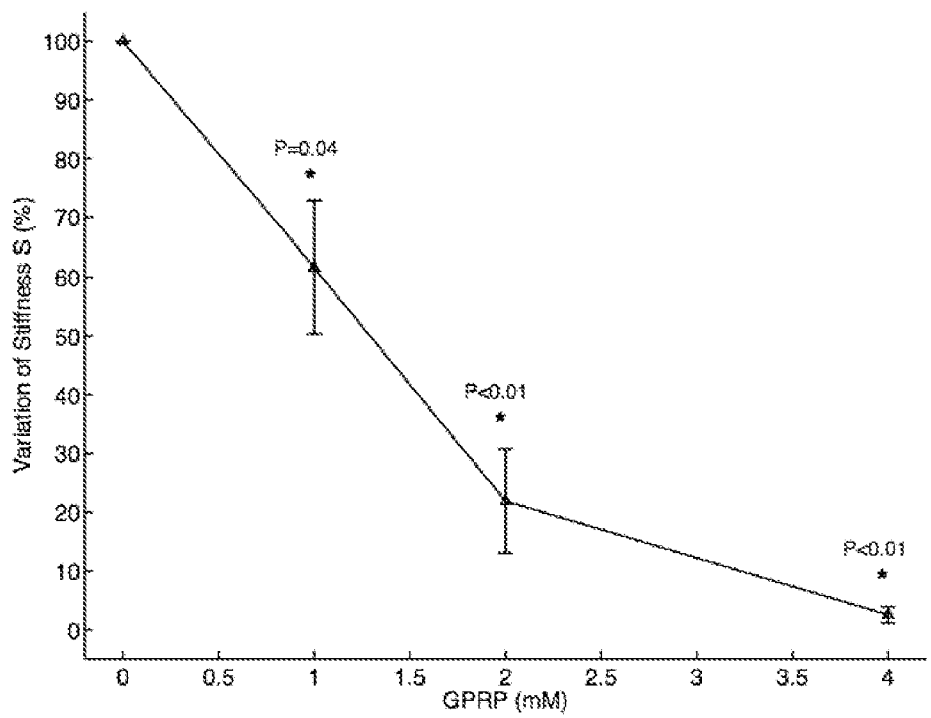
FIG. 13 is a plot showing stiffness.

These experiments were performed to characterize the function of the plasma coagulation factors and the consequent generation of a viscoelastic fibrin structure using sonorheometry. Fibrin is the building block of blood clots. Blood samples from 5 volunteers were obtained and the Gly-Pro-Arg-Pro (GPRP) peptide was added in titrated quantities to achieve final concentrations of 0, 1, 2, 4, and 8 mM. GPRP is a strong inhibitor of fibrin polymerization that blocks the sites located in the ⓒ chains at the two D end domains of the fibrinogen molecule, as described in further detail by Laudano et al., *Studies on synthetic peptides that bind to fibrinogen and prevent fibrin polymerization. Structural requirements, number of binding sites, and species differences*. Biochem 1980; 19:1013-1019. Increasing concentrations of GPRP produced distinctive changes in mechanical properties, as shown in the sonorheometry stiffness curves in FIG. 10, which correspond to GPRP concentrations of 0, 1, 2, 4, and 8 mM, respectively. Both initial and final clotting times $TC_1$ and $TC_2$ increase with the concentration of GPRP, as shown in FIG. 11. These results suggest that $TC_1$ and $TC_2$ are representative of the beginning and ending phases of fibrin polymerization caused by the coagulation factors in the plasma. Significant changes were also observed for both the clot formation rate CFR (FIG. 12) and the stiffness S (FIG. 13) with increases in the concentration of GPRP. As expected, the process of fibrin polymerization was a key component in determining the dynamics of clot formation and clot stiffness. Increasing levels of GPRP decreased both the rate of fibrin polymerization and the final stiffness of the formed clot.

Assessment of Platelet Function

Platelets play various important roles during hemostasis. These complex functions include: adhesion to the site of injury, activation and shape change, secretion of internal granules to recruit additional platelets, aggregation with surrounding platelets via fibrinogen links, interaction with fibrin mesh, and clot retraction in order to reduce the volume of the clot, see also Carr, "In Vitro Assessment of Platelet Function", Trans. Med. Review 1997; 11:106-115 and Packham, "Role of platelets in thrombosis and hemostasis", Can. J. Physiol. Pharmacol. 1994; 72:278-284. Of particular importance is the mechanism of aggregation, which ultimately determines the ability to form a platelet plug that can stop bleeding. Aggregation is mediated by fibrinogen that binds to the glycoprotein (GP) IIb/IIIa, forming bridges between adjacent activated platelets. Experiments were performed to investigate the contribution of platelets on sonorheometry measurements. Titrated quantities of monoclonal antibody abciximab were added to blood samples from five individuals to achieve final concentrations of 0, 2, 4, 6, 8, and 12 µg/ml. Abciximab is a potent inhibitor of platelet aggregation that prevents platelets from binding to fibrinogen by blocking the IIb/IIIa receptor on the platelet's surface, see The EPIC Investigators, "Use of monoclonal antibody directed against the platelet glycoprotein IIb/IIIa receptor in high-risk coronary angioplasty", N. Engl. J. Med. 1994; 330:956-961 and Collier et al., "A murine monoclonal antibody that completely blocks the binding of fibrinogen to platelets produces a thromastenic-like state in normal platelets and binds to glycoproteins IIb and/or IIIa", J. Clin. Invest. 1983; 72:325-338.

Figure 14:
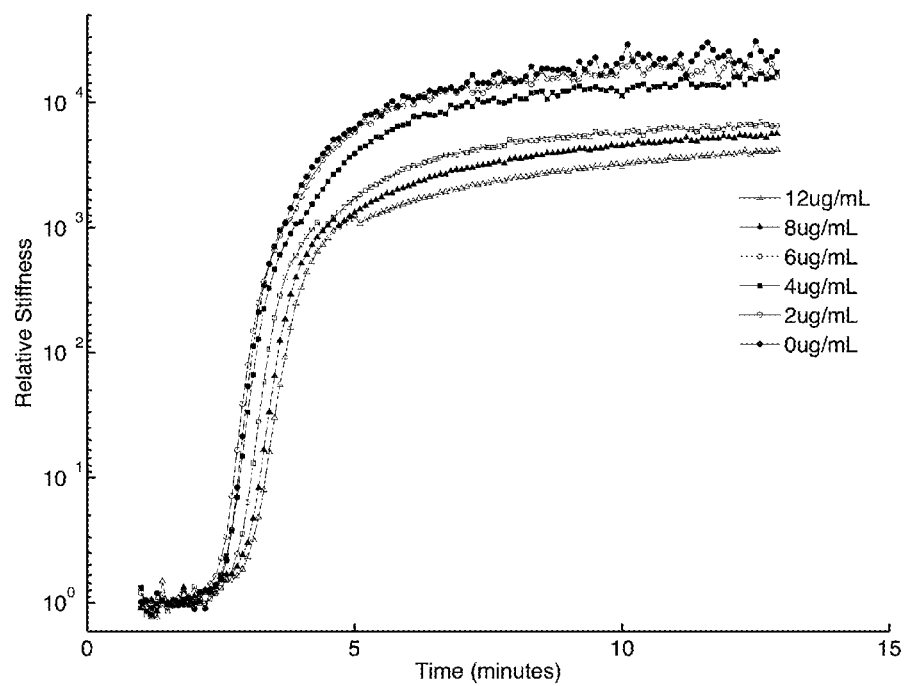
FIG. 14 is a plot showing the effect of concentrations of abciximab.
Figure 15:
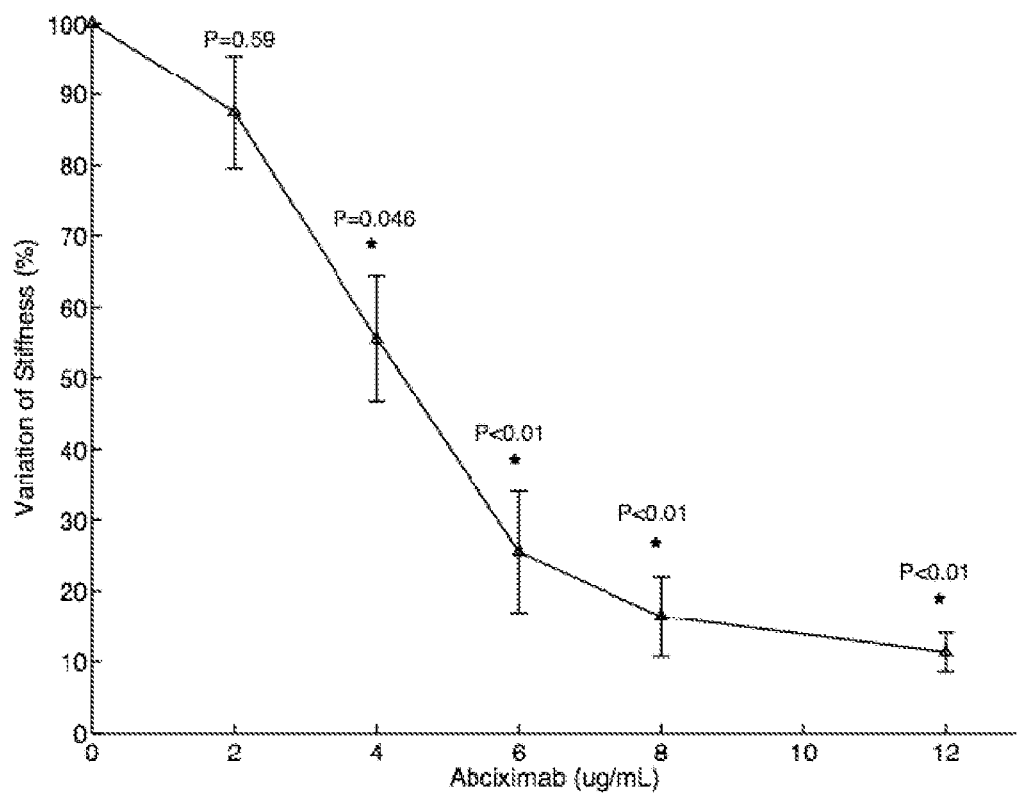
FIG. 15 is a plot showing percentage changes of $S_{MAX}$ as a function of abciximab concentration

The resulting sonorheometry curves demonstrate that increasing inhibition of platelet aggregation reduces the stiffness $S_{MAX}$ yielding a softer clot, as shown by curves in FIG. 14, which correspond to concentrations of abciximab in the samples of 0, 2, 4, 6, 8, and 12 µg/ml, respectively. The other parameters describing the dynamics of clot formation and dissolution did not change significantly, but fell within the intrinsic variability. Final clot stiffness varied by over one order of magnitude across the concentrations used for this experiment. FIG. 15 shows percentage changes in $S_{MAX}$ as a function of abciximab concentration.

The results of the experiments and plots shown in FIGS. 14 and 15 suggest that the final stiffness of the clot resulted from the interaction of aggregated platelets and fibrin network. The stiffness parameter $S_{MAX}$ is thus indicative of the combined mechanical functions of the fibrin network and the platelet aggregation/contractile function. The ability of sonorheometry to characterize platelet aggregation is thus useful, for example, to determine the efficacy of therapies based on Plavix® or non-steroidal anti-inflammatory drugs (NSAIDs) and to discriminate responders from non-responders to these drugs.

Assessment of Fibrinolytic Proteins

Experiments were performed to assess fibrinolysis using sonorheometry. For this set of experiments, titrated amounts of urokinase type plasminogen activator were added to the samples. Urokinase type plasminogen activator is a serine protease that promotes dissolution of the fibrin network that forms the blood clot, see Lijnen et al., "The mechanism of plasminogen activation and fibrin dissolution by single chain urokinase-type plasminogen activator in a plasma milieu in vitro", Blood 1989; 73:1864-1872. Total amounts of urokinase were 0, 100, 150, and 200 Units per ml of blood, respectively. Urokinase shows significant effects on the measurements performed by sonorheometry, as indicated by the relative stiffness curves in FIG. 16 that correspond to total amounts of urokinase of 0, 100, 150 and 200 Units per ml of blood sample, respectively. The blood samples returned to a viscous fluid significantly faster with increasing concentrations of urokinase, as expected. Both clot lysis times $TL_1$ and $TL_2$ decreased as a function of urokinase concentration, as illustrated in FIG. 17.

Figure 16:
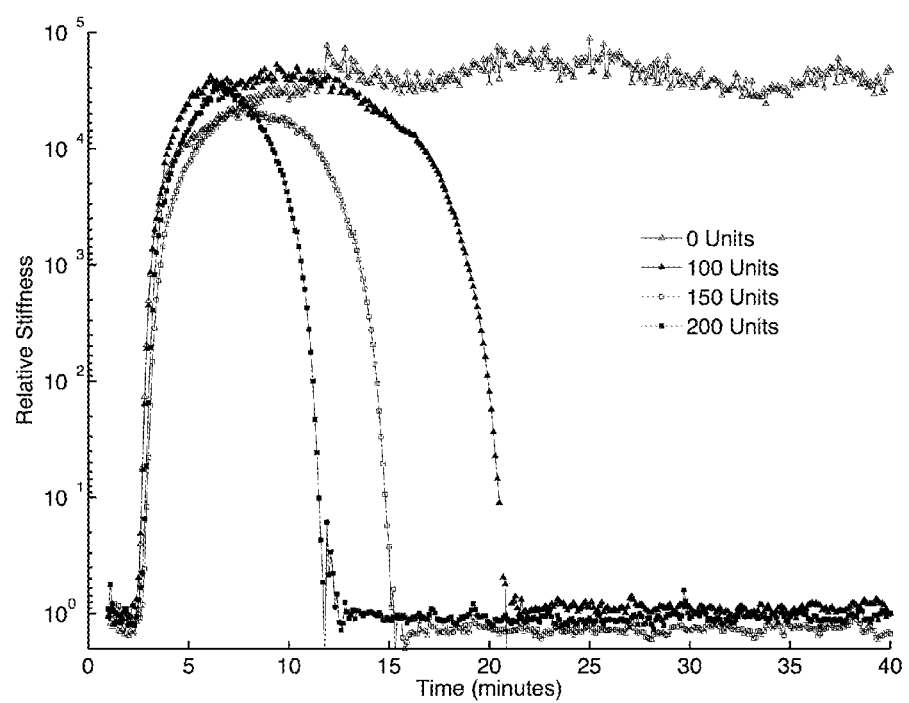
FIG. 16 is a plot showing relative stiffness as a function of urokinase concentration.
Figure 17:
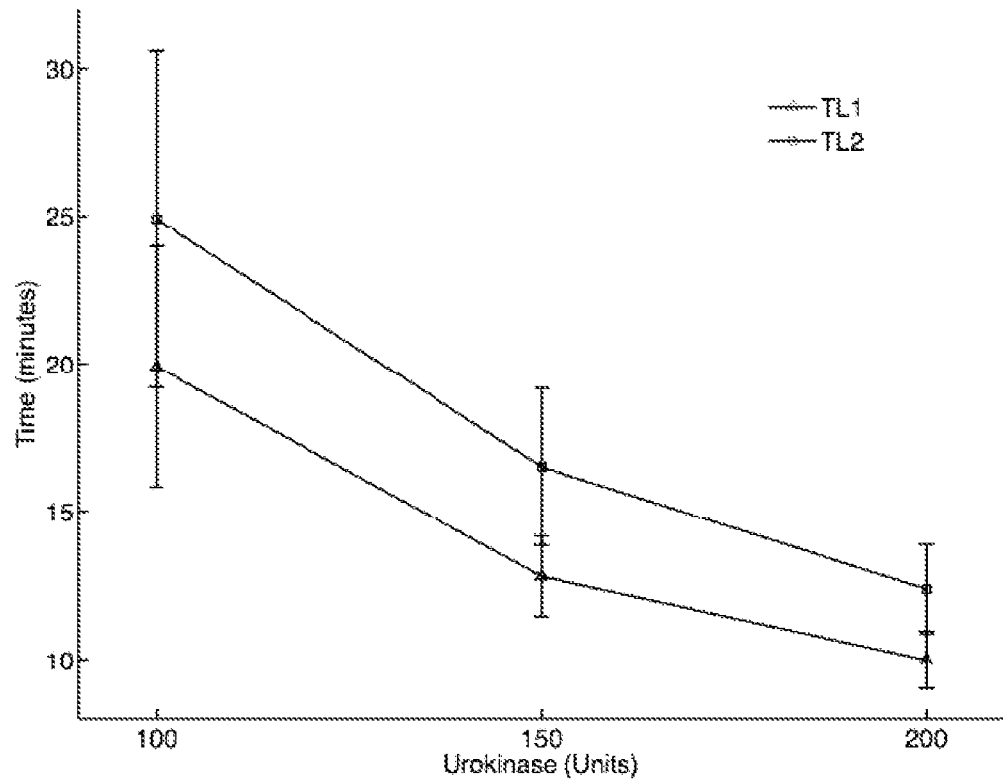
FIG. 17 is a plot showing effect of urokinase on clot lysis times.

FIGS. 16 and 17 show that the increased fibrinolytic activity caused by urokinase rapidly dissolved the blood clot and restored the original mechanical conditions prior to clot formation. The results in FIGS. 16 and 17 suggest that the parameters $TL_1$ and $TL_2$ can be used to characterize dysfunctions of the fibrinolytic system, such as in the case of hyperfibrinolysis.

Reproducibility Error of Repeated Sonorheometry Measurements

The intrinsic variability of sonorheometry was tested using whole blood samples from five volunteers. For each subject, ten samples were obtained into 1.8 ml Vacutainers (with 3.2% sodium citrate) and analyzed sequentially using kaolin activation. The estimated coefficients of variation were below 6% (averages over the five subjects) for all of the parameters described above, except $LT_1$ and $LT_2$ (the coefficient of variation for $LT_1$ and $LT_2$ were not estimated since clot lysis was not observed within the experiment time of fifteen minutes).

II. Determination of HCT and Associated Parameters

Despite the success of the above-described embodiments, the inventors have learned that measurement of whole blood parameters for characterizing clotting can be dependent upon or affected by the hematocrit (HCT) of the measured sample. Other embodiments of the present invention account for the impact of HCT by having integrated therein the capability to additionally quantify HCT and related parameters for use in correcting or adjusting clotting parameters measured by the above-listed embodiments.

An integrated ultrasonic system of the present invention can provide measurements of HCT, hemoglobin concentration (HGB), mean corpuscular volume (MCV), red cell count (RBC), total protein concentration (TPC), mean cellular hemoglobin (MCH), and mean cellular hemoglobin concentration (MCHC) and use those measurements for correcting or adjusting clotting parameters. These parameters are referred to collectively herein as oxygen transport parameters which are any parameters that characterize a fluid's ability to transport oxygen throughout an organism.

Ultrasound measurements of HCT and related parameters may include backscatter—measuring energy reflected from a blood sample, attenuation coefficient—measuring energy attenuation per unit length through a blood sample, speed of sound—measuring the speed of sound through a blood sample, frequency analysis—measuring the response of the blood chamber to ultrasound at more than one frequency.

The HCT and related parameter aspect of the embodiment sends one or more ultrasonic signals to a blood sample; senses and analyze the echoed sound; calculates backscatter coefficients, speed of sound, and/or attenuation coefficient for frequencies of interest; determines one or more of HCT, MCV, HGB, TPC using the correlations that relate speed of sound, attenuation coefficient, frequency and/or backscatter coefficients to said blood properties. From these results, the values of RBC, MCH, and MCHC may be calculated, in some cases depending upon availability of another parameter, using the definitions RBC=HCT/MCV, MCH=HGB/RBC, and MCHC=MCH/MCV.

The equipment preferably includes, or duplicatively uses from the prior embodiments, an electronics subsystem and a hardware subsystem. The electronics generate the signal burst and record and analyze the resulting echoes. The hardware contains the sample and maintains alignment of the various components.

Preferably, the HCT measurement aspect of the apparatus includes, or duplicatively uses from the prior embodiments, a sample collection mechanism, sample chamber, transducer, transducer coupling to the sample, and automated signal processing.

Hematocrit is defined as the volume fraction of red blood cells in a sample of blood. The speed of sound in blood is a direct function of the hematocrit (HCT) and a direct function of the amount of hemoglobin in the blood (HGB). This relationship arises because red blood cells and hemoglobin have different material compositions from the surrounding plasma and therefore different speeds of sound. The speed of sound of whole blood is approximately the bulk average of the speeds of sounds of its components. In other words, the higher the concentration of red blood cells, the more the speed of sound of the blood will approximate that of red blood cells instead of plasma. Because red blood cells make up nearly 50% of the blood volume, HCT and HGB are by far the strongest drivers the speed of sound. Variations of other blood components (white blood cells, platelets, extra-cellular proteins) may change the speed of sound slightly and limit the accuracy of the measurements, but their influence is small enough that it has not been identified in experiments to date.

Since the majority of the hemoglobin is in the red blood cells under normal physiological conditions, the HGB and HCT results typically provide equivalent information to the physician. They both indicate the oxygen-carrying capacity of the blood.

$$Cf = g(HCT, T) \qquad (14)$$

$$Cf = f(HGB, T) \qquad (15)$$

Where Cf is the speed of sound in blood, HGB is concentration of hemoglobin, HCT is hematocrit, T is temperature, and f and g are functions that can be determined empirically.

Because speed of sound is a function of HGB and HCT, one can measure speed of sound and apply it as an indication of the HGB and/or HCT by inverting the calculation.

Similarly, the attenuation coefficient in blood is a direct function of the HGB and HCT of the blood because ultrasound attenuates to different degrees in red blood cells than it does in pure hemoglobin or in plasma. This attenuation is caused in part by the viscous losses in the various substances that make up whole blood. The attenuation is also caused in part by the ultrasound scattering off material boundaries such as the membranes of red blood cells. For this reason, the attenuation is also a function of the MCV of the blood, although the relationship is weak enough that in some cases it may be neglected.

$$\alpha = f(HCT, MCV, T, F) \approx f(HCT, T, F) \qquad (16)$$

where $\alpha$ is attenuation coefficient, HCT is hematocrit, MCV is mean cellular volume, T is temperature, F is frequency, and f is a function that can be determined empirically.

For embodiments in which the relationship between attenuation coefficient and MCV can be neglected without sacrificing excessive accuracy, redundant measurements can be made. Attenuation coefficient and speed of sound can both be used to independently calculate hematocrit and hemoglobin concentration. Then, the two calculations can be compared for error detection and/or averaged to improve accuracy. Alternatively, the two measurements can be used together to eliminate another common variable such as the distance the sound travels in blood or temperature.

Backscatter is the acoustic energy reflected from blood. Since this reflection originates almost entirely from scattering off the red blood cells, the backscattered energy is a complex function of the MCV and HCT of the blood sample. However, the function is only monotonic and well behaved for HCT levels below 15%. Preferably, to use backscattered energy to accurately determine MCV and HCT of a sample, the blood sample first can be diluted to bring the HCT into the linear region below 15% then the device preferably compensates for the dilution in its calculations.

$$Bks = f(HCT, MCV, T, F) \quad (17)$$

where Bks is backscattered energy, HCT is hematocrit, MCV is mean cellular volume, T is temperature, F is frequency, and f is a function that can be determined empirically. It should be noted that scattering is a "noisy" parameter and may be difficult to measure while speed of sound is a clean measure. Attenuation occurs between the two.

By measuring the ultrasonic backscatter coefficient and using a correlation to HCT, one can determine the HCT of the diluted sample, and thus the hematocrit of the original sample. The backscatter method can also be used in an undiluted sample though the relationship is more complicated. One motivation for measuring backscatter on an undiluted sample is to determine the blood parameters non-invasively by sending and receiving ultrasound into the body.

In one embodiment, the method includes subjecting a whole blood sample to one or more ultrasonic pulses, then measuring the ultrasonic characteristics listed above: (a) backscatter from the blood sample, (b) attenuation of the ultrasonic pulse through the blood sample, or (c) the speed of sound through the blood sample. The measurement of (a), (b) or (c) can be used alone or in combination to determine one or more of the related clinical parameters: HCT, HGB, MCV, RBC, MCH, MCHC, TPC.

The preferable way to calculate speed of sound is by measuring the time of flight of short ultrasonic pulses over a known distance.

$$Cf = d/t \quad (18)$$

where Cf is the speed of sound, d is the distance the sound travels through the sample, and t is the measured time it takes for the sound to travel that distance.

The time between transmission and reception is usually considerably longer than the transit time through the sample because it includes delays in the electronics and delays as the ultrasonic wave passes through materials not being studied such as the container walls. Preferably, the transit time through the sample is not measured directly but instead is determined as the difference between two other measurements: the total transit time (which includes both time in the blood and undesired delays) minus the transit time through only undesired delays.

$$t_{blood} = t_{total} - t_{delays} \quad (19)$$

where $t_{blood}$ is the transit time the ultrasound takes to travel through the sample, $t_{total}$ is the measured time from send to receive including undesired delays, and $t_{delays}$ is the measured time of all delays except for the transit through the sample.

Figure 6:
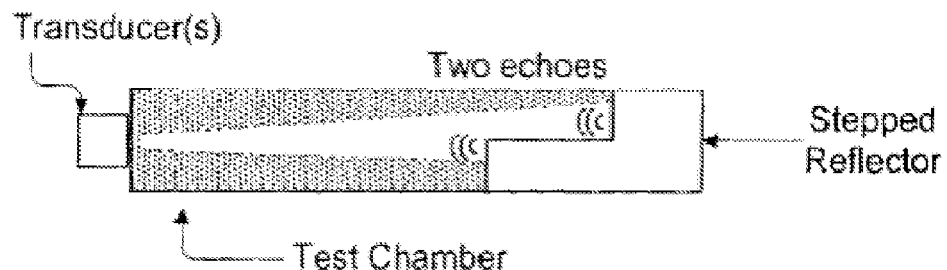
FIG. 6 is a schematic of a two-reflector system for determining HCT and similar blood parameters.

One preferable way to measure this time difference is to measure the round trip times of flight from two or more reflectors separated by a known distance along the axis of flight (see FIG. 6). The ultrasound is broadcast in one beam. A portion of the ultrasound echoes from the closer reflector while the rest of the beam continues traveling to echo off the second reflector. The difference between these round trip times, divided by two times the distance between reflectors, is the speed of sound in the sample.

Figure 8:
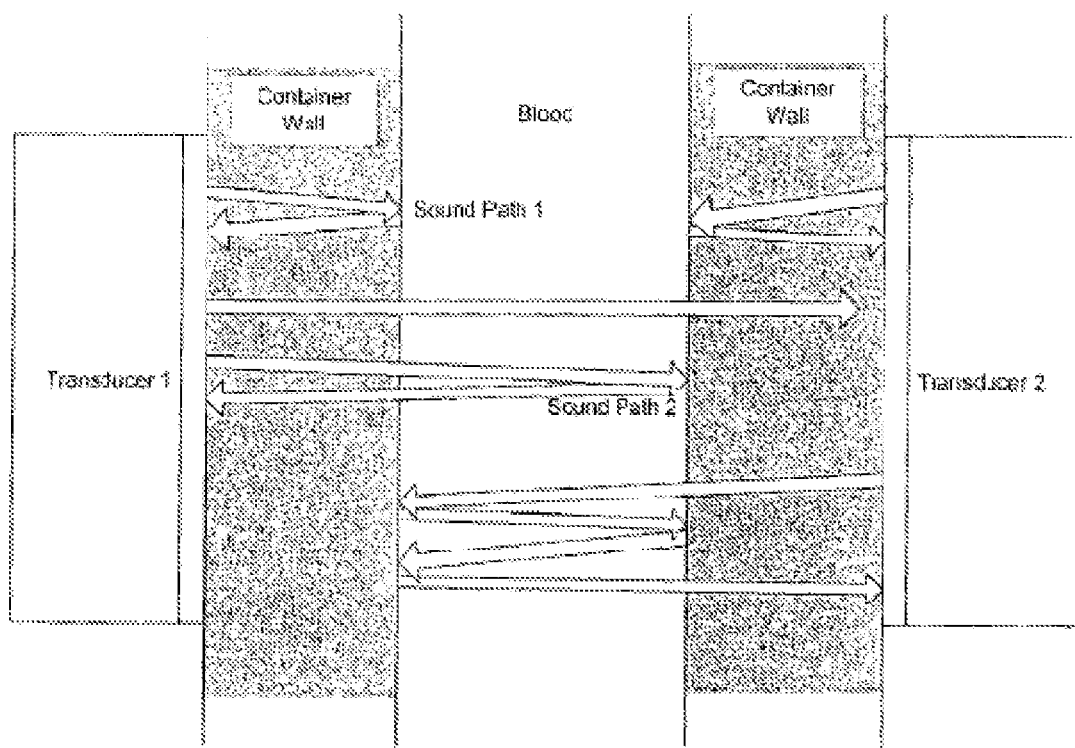
FIG. 8 is a schematic of a two-transducer system for determining HCT and similar blood parameters.

Another preferred embodiment uses a chamber of a precisely known size through which transducers send pulses in pitch-catch mode (see FIG. 8). Using pulse-echo measurements from the edges of the chamber allows subtraction of all time delays except the time the sound spent traveling through blood.

In another preferable embodiment, the blood is in a flexible chamber, and time-of-flight measurements are made both before and after deforming the chamber by a known or measurable distance. In another embodiment, the blood is in a flexible container that fills the space between two precisely located walls. The container material is well controlled such that its time delay is well known and can be subtracted. Preferably, the speed of sound through this flexible wall is roughly matched to the speed of sound through blood, so that the error caused by inaccuracies in estimating the thickness of the wall will negligibly affect the transit time.

Temperature affects speed of sound, attenuation coefficient, and backscatter so the results are preferably adjusted to account for temperature, such as by using the embodiments described above. Furthermore, depending on the materials selected, it may need to account for temperature affects on the sizes and shapes of its component parts.

The technique used to measure the attenuation coefficient in blood is similar to the technique used to measure speed of sound. The RMS amplitude of the reflections is measured. If a known reflector, the absolute amplitude of the echo will be measured. The ratio of the amplitudes from two paths through blood of different lengths is expressed in decibels and divided by the difference of the path lengths.

$$A = 20 \operatorname{Log}(V2/V1)/(D2 - D1) \quad (20)$$

where A is the attenuation coefficient in dB/in, V2 and V1 are the amplitudes of the two received signals, and D2 and D1 are distances the two signals traveled through the sample.

The speed of sound data and the attenuation coefficient data are usually collected at the same time for each sample. Furthermore, the calculations can be compensated for the temperature of the blood and frequency of the signals.

The backscatter measurement is performed by analyzing the ultrasonic echo from a diluted blood sample and measuring the RMS voltage of a specified time window within the returned signal. The transducer preferably generates a burst containing 2-10 cycles of the center frequency of the interrogating transducer. Energy is reflected back from blood-chamber interface, followed immediately by the energy scattered back by the components of the blood sample. By time gating the RMS measurement to measure the energy scattered by only the sample, and averaging over 50 sampled signals or more, the average backscattered power is measured.

The clinical parameters (HCT, HGB, MCV, RBC, MCHC, MCH or TPC) may also be determined by exciting the chamber with continuous waves. The frequency of this continuous wave is varied slowly to analyze the response of the blood at each frequency. At the resonant frequency, a standing wave is set up which indicates that the wavelength is directly related to the chamber's dimensions. Determining the resonant frequencies allows one to calculate the wavelength and correlate that to hematocrit. Furthermore, the bandwidth (i.e., fill width at half-maximum) of the resonant frequency peaks is effectively another indication of attenuation. The wider the frequency peak, the higher the attenuation coefficient. Other related ultrasonic measurements that provide similar information include the phase shift or amplitude of the signal.

Acoustic impedance is also an indicator of hematocrit and/or hemoglobin because the acoustic impedance of hemoglobin and other blood constituents is higher than the acoustic impedance of pure plasma. Therefore, higher concentrations of hemoglobin and red blood cells will increase the acoustic impedance of the overall substance from that of pure plasma. Acoustic impedance can be calculated by measuring how much ultrasound is reflected from an interface. If the acoustic impedance of the blood matches the acoustic impedance of the container wall, then no ultrasonic energy will be reflected from the interface. The more the mismatch of acoustic impedances, the more energy will be reflected from the interface. The apparatus preferably lyses the red blood cells before implementing this method to ensure that the hemoglobin and other blood constituents are evenly distributed throughout the blood and along the material interface being used to measure acoustic impedance.

Another ultrasonic measurement that indicates the physiological parameters is refraction angle. The refraction angle of the ultrasonic wave at a material interface is an indicator of speed of sound as shown by Snell's Law. Therefore, refraction angle will be directly affected by the physiological hematocrit and/or hemoglobin. One preferred way to implement the refraction measurement is to send ultrasound through a triangular blood container that acts as a "prism." The ultrasonic wave enters the blood perpendicular to the container surface. But, because of the triangular shape of the container, the ultrasound strikes the far wall of the chamber at a known angle of incidence. According to Snell's law, the wave will then travel through the container wall at a angle that depends on the speed of sound in the blood. Measuring that angle (preferably using a steered array transducer) allows the apparatus to back-calculate the speed of sound in the blood use an empirical correlation to calculate the hematocrit and/or hemoglobin.

$$\text{Snell's Law: } \sin(\theta_1)/C_1 = \sin(\theta_2)/C_2 \qquad (21)$$

where $\theta_1$ is the angle of incidence, $C_1$ is the speed of sound in material 1, $\theta_2$ is the angle of refraction, and $C_2$ is the speed of sound in material 2

Figure 5:
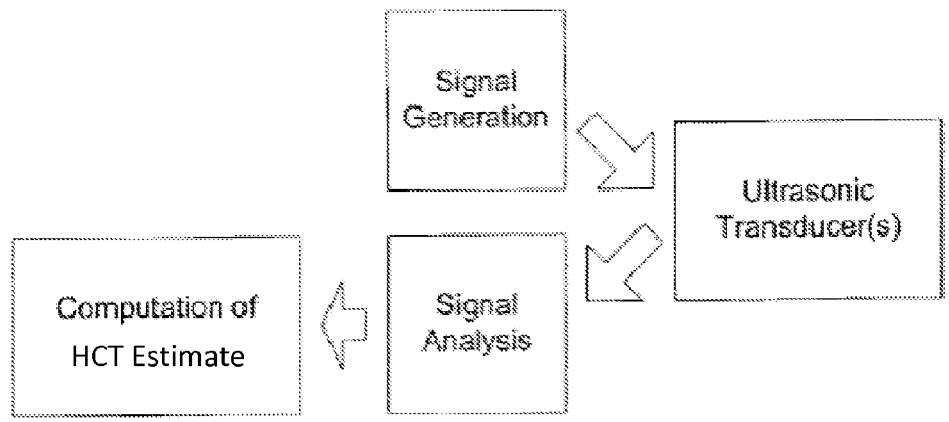
FIG. 5 is a schematic of electronics for a system for determining HCT and similar blood parameters.

The electronics preferably include means for signal generation, signal capture, and analysis. Preferably, the electronics are responsible for four functions (shown in FIG. 5): generating a precisely controlled signal, sending and receiving the ultrasonic waves, analyzing the received waves, and computing the clinically-relevant results. These functions are divided into the input stage and the receiving stage. Each stage may exist as a separate device, or preferably, some or all of the stages may be integrated together as a single component.

The sending stage preferably includes a programmable signal generator, signal conditioning components (to amplify, filter, and/or reduce noise), and a power amplifier. The signal generator functions to generate one or more acoustic signals. The signals may be a gated sinusoid, square pulse, spike with exponential delay or other function. The signal normally would have a center frequency matched to the center frequency of the transducer in use to maximize the amount of energy delivered to the sample. For frequency sweeps, the frequency range is preferably chosen to lie within the usable bandwidth of the transducer.

The pulse generator will preferably generate an electronic pulse to operate the transducers in pitch-catch or pulse-echo mode. The frequency of the signal may be from 1 to 50 Mhz, preferably from 5 to 20 Mhz, depending on the type of measurement being made. Higher frequencies could be chosen if the sound is only traveling a short distance through blood in order to increase time resolution or to achieve wavelengths proximate in length to a red blood cell diameter. Lower frequencies could be chosen for long paths to minimize attenuation. The burst length may, for example, be 0-5 cycles, most particularly preferably 1-2 cycles for speed of sound and attenuation coefficient measurements. The amplitude of the signal generator is preferably maintained at a setting sufficient to provide high-signal-to-noise ratio.

The signal from the input stage is passed to the transducer. The transducer(s) are preferably high efficiency, single element transducers. A variety of commercially available transducers are suitable for use in the apparatus. Each transducer may be selected to match the chamber geometry based on the center frequency, bandwidth, focusing, sensitivity, and beam pattern. For backscatter measurements, the range of frequencies is selected to include values both above and below the 15 MHz threshold for Rayleigh scattering. Preferred interrogating frequencies include 6.5, 10, 20, 30, and 40 MHz. In general, higher frequencies are preferable if the sound is only traveling a short distance through blood in order to increase time resolution and narrow the acoustic beam. Lower frequencies are preferable for long paths to minimize attenuation.

For all configurations and measurements, the transducer element diameter is preferably selected to ensure that the beam angles are appropriate for the shape of the chamber. The beam widths should be narrow enough to minimize the chance of undesired sound paths interfering with the measurement. Furthermore, the element diameter affects the distance the transducer can be from the sample (far field distance). Focused transducers may help reduce beam width and far-field distance. Some preferred transducer diameters include 3 mm, 6 mm, and 12 mm. The transducers may be used in pulse echo mode and/or in pitch catch mode depending on how they are arranged relative to the chamber. Measuring the time difference between paths or between these two operating modes can eliminate unknowns such as the delays in the electronics or sample holder. An annular array of transducers could be used to enable a deeper depth of field.

Figure 7:
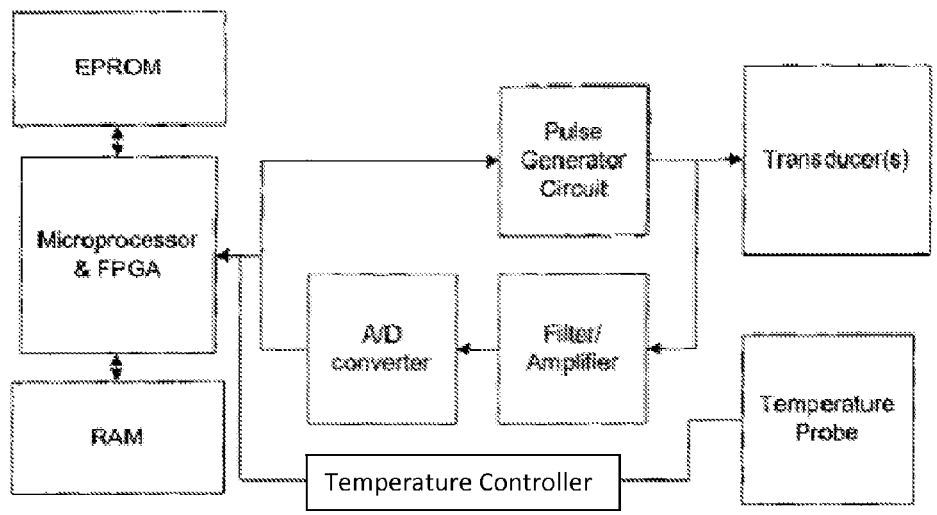
FIG. 7 is a schematic of components of a system for determining HCT and similar blood parameters.

The signal returned from the sample causes the transducer to generate an electrical signal that is passed along to the receiving stage. The receiving stage preferably includes signal conditioning, an amplifier, a digitizer, and a means for collecting and analyzing data, such as a microprocessor or microcontroller and RAM, magnetic storage or CD (see FIG. 7). In this configuration, signal measurements and calculations including transit times and amplitude are calculated based on the digitized signal by the microprocessor.

Another preferable receiving stage configuration includes signal conditioning, an amplifier, an analog peak detect circuit and a timing circuit. The peak detect circuit is used to measure the signal peak amplitude and the timing circuit is used to determine the time from signal transmission to receipt.

The amplifier is used to bring the signal amplitude up to a level that can be readily captured by a digitizer and/or analyzed by analog electronics. Therefore, the amplifier should be chosen to have the needed gain. The amplifier should also be chosen to have the appropriate bandwidth for the planned measurements. The amplifier(s) may also include one or more filters built-in. The filters are used to eliminate noise that lies outside the frequency band being measured. Suitable filters include active and passive filters, RC filters.

The HCT detection aspect also preferably includes appropriate device control, signal processing and detection logic.

Device control may be through an on-board processor, programmable logic controller or through discrete logic blocks. The signal processing algorithms preferably include one or more of the following: analog and digital noise filtering, averaging, gating and automatic gain control. Detection logic may include zero-crossing detection, which automatically measures the exact time a signal crosses zero in order to calculate the transit time of a signal, and amplitude or power measurement. A time delay estimation method, similar to that used for motion estimation under radiation force, could also be used.

Hardware preferably includes the sample chamber and transducer. The sample chamber or holder is designed to contain the blood sample, allow for stirring of the sample (in the case of backscatter measurements), and maintain alignment and distance between the transducer and the sample. Stirring could be performed by using high intensity pulses to generate acoustic radiation force induced streaming. In some embodiments of the apparatus, the chamber is actually a segment of a tube through which the blood flows continuously (ex-vivo). In other embodiments the chamber is made of flexible materials such as rubber so the blood sample's size or shape can be controlled or adjusted. Alternatively, the blood chamber may comprise the patient's body itself in the case of an in-vivo or non-invasive measurement.

The collection means includes allowances for making live blood draws. The collection method may be an off the shelf syringe, off the shelf lance, or custom device which acts as a collection device and a sample chamber combined. Furthermore, the chamber may be a tube through which the blood flows.

The sample chamber is preferably disposable and compact. Preferred sample chamber materials include glass, polystyrene, polyamide, polyvinylchloride, silicone, polypropylene, latex or polyethylene. The chamber and/or added reflectors (if used) are preferably manufactured to precisely known dimensions so that the sound path length is preferably known to +/−0.2%, more preferably to +/−1-0.05%, which ranges include +/−0.15, 0.125, 0.1, 0.09, 0.075, and 0.065%. A precisely-known path length is preferred to more accurately calculate speed of sound from measuring the time of flight. If the chamber cannot be accurately manufactured, then the path length is preferably measured either by the apparatus itself or by an independent device. The results from said independent device would preferably be fed into the apparatus automatically by a means such as barcodes.

The sample chamber and/or apparatus parts in acoustic contact with the blood and/or sample chamber preferably has a speed of sound matched to the speed of sound in blood between 1000 m/s and 2500 m/s, which range includes 1200, 1400, 1600, 1800, 2000, 2200, and 2400 m/s. Preferable materials include plastic, rubber, aluminum, and combinations thereof.

The sample chamber preferably holds 0.05 to 10 mL of blood, which range includes 0.075, 0.1, 0.3, 0.5, 0.7, 0.9, 1, 2, 3, 4, 5, 6, 7, 8, and 9 mL of blood.

The temperature of the sample may be measured directly or indirectly. Indirect means may include waiting for the sample to equilibrate with its environment and measuring the ambient or container temperature in lieu of the blood temperature. If the temperature of the blood is changing rapidly (because it has been freshly drawn for example) repeated ultrasonic measurements allow the apparatus to infer a trend and predict what the final readings would be once the sample has reached thermal equilibrium with its surroundings. Since speed of sound in any apparatus or container changes with respect to temperature, the temperature of the container walls can be inferred by measuring the speed of sound through the walls. The temperature may also be controlled (such as by a temperature controller shown in FIG. 7) so that no temperature variations affect the measurement.

The sample chamber and collection means can also be combined into a single component, wherein the blood sample is collected in the collection means, which then acts as the sample chamber upon which the ultrasound method is used. Further, the collection means and sample chamber may comprise a tubular arrangement such that the blood is collected from the patient using a venipuncture needle or other needle device, whereupon the blood flows through a length of tubing. The length of tubing can act as the sample chamber, particularly for the attenuation coefficient and speed of sound measurement methods performed on a sample flowing through the length of tubing. Backscatter based methods are less desirable using a flowing sample due to movement of the red blood cells through the tube. In any event, a calibration can be obtained using samples of independently measured hematocrit, permitting the measurement of the HCT, MCV and/or RBC of the sample, even when flowing through the sample chamber.

One preferred sample chamber embodiment includes a single or dual element transducer that projects beam(s) through the blood sample, returning reflections from a stepped reflector at the other end of the sample chamber (see FIG. 6). The difference in round trip time from these steps can be used to calculate the speed of sound in the test sample.

The stepped reflector design is preferred in that it has no moving parts, and it is not susceptible to variable time delays outside of the sample chamber, such as transducer couplant delay.

Another preferred sample chamber includes a small chamber with rigid parallel walls and a depth such that only a few drops of blood can fill the chamber. Sound is transmitted through the chamber along a path perpendicular to the walls as in FIG. 8.

Another preferred sample chamber consists of a rubber bladder. This is configured such that when it is placed in the electronics unit and filled with blood, it expands to fill the space between a single fixed transducer and a reflector or between two fixed transducers in the electronics unit.

The reflector could be inside the chamber or outside. Most preferably, the chamber shape itself would act as the reflector for ease of manufacturing. The material of the reflector is not particularly limited. The path length difference is likewise not particularly limited, and could preferably range from 1 mm to 10 cm, which range includes 2, 3, 4, 5, 6, 7, 8 and 9 mm, and 1, 2, 3, 4, 5, 6, 7, 8, and 9 cm. Longer paths are preferred for making a more accurate measurement, but shorter paths require less blood. Moving reflectors are possible. In all configurations, vertical ultrasound paths are preferred so that if the red blood cells settle, their average concentration in the beam remains constant.

In the case of a horizontal beam, the cells could settle preferentially into or out of the beam causing an erroneous reading. Or, different portions of the beam could pass through different concentrations of cells causing a distorted answer. In the same way, a vertical sound path ensures that even if thermal stratification occurs, the ultrasound will travel through all the temperature layers of the blood instead of preferentially measuring through a warmer or colder region. The transducers may use liquid or grease as an acoustical couplant to a solid blood container, may be coupled directly to the sample container (dry coupled), or may transmit sound directly into liquid or gas instead of a solid. The transducers may be held in a fixture to ensure reliable acoustical coupling to the sample. In one preferred embodiment, the transducers are disposable and built into the sample chamber. When disposable transducers are integrated into a disposable chamber, the chamber is preferably connected to the test device electrically instead of acoustically.

The transducers are preferably narrow beam width and more preferably focused to avoid coherent noise caused by stray reflections depending on the geometry of the sample chamber. Preferably, transducers having center frequencies of approximately 1 MHz to 50 MHz, more preferably 5 to 20 MHz may be used. 10 MHz transducers are most preferred, however. The higher frequency transducers accommodate a shorter path length and more precise timing. A pair of transducers are most preferably used, one on each side of the collected sample as in FIG. 8.

Three types of test chamber are preferable for this device and they all use a drop or several drops of blood. The fact that they use a few drops of blood limits the size of the chamber accordingly. The first will be a small capillary tube, preferably capped at one end. This type of tube is similar or identical to that currently used in medical settings as part of a microhematocrit test. The second preferred embodiment is a sample card, which collects a drop of blood in a small rectangular hole to through which ultrasonic measurements can be made. The third preferred embodiment is a sample card, which collects a drop of blood in a flexible thin walled chamber that fills the space between two precisely-located walls within the meter. Also, a cartridge could be used with predefined wells configured for sample filling using suction, such as the preferred cartridge disclosed in U.S. patent application Ser. No. 13/397,398 filed on Feb. 15, 2012 and entitled DEVICES, SYSTEMS AND METHODS FOR EVALUATION OF HEMOSTASIS which is incorporated by reference herein in its entirety. This application also discloses preferred hardware and processes for determining hemostasis parameters using multiple samples with different reagents.

The transducers in this preferred embodiment are preferably in the 10 to 100 MHz range, more preferably 20 MHz. Though the measurement can be made with only one transducer, a pair is most preferably used, one on each side of the collected sample. Locating the pair in this fashion allows both pitch-catch and pulse-echo signals to be measured as shown in FIG. 8. The fixture holding these transducers preferably ensures reliable acoustic coupling between the sample chamber and the transducers.

The signal generator generates a simple electronic signal of sufficient duration and amplitude to operate the transducers. The frequency of the signal is appropriate for the selected transducer, and is preferably from 1 to 3 cycles in length. The amplitude of signal should be as high as possible without exceeding the transducers' ratings. Another amplifier circuit may be needed to maximize the signal-to-noise ratio. With the appropriate electronics (discussed above) this hardware can also determine the relevant clinical parameters using other measurements such as measuring the frequency response of the chamber to determine how much it resonates at each frequency.

Device control may be through an on-board processor, or through a programmable logic controller that may be shared with the other embodiments for determining clotting parameters. The signal processing algorithms preferably include one or more of the following: noise filtering, averaging, and automatic gain control. Detection logic preferably includes zero-crossing detection. Zero-crossing detection is a method for accurately measuring the time at which a signal like a wave burst arrives. In this method, the wave is timed by detecting precisely when the signal crosses zero. Because most typical bursts last several cycles and therefore cross zero multiple times, a single crossing is preferably used consistently in a given application of the method. For example, one embodiment is to use the 2nd (or 3rd or 5th) zero crossing of every burst as the consistent timing point.

A spline based method or principal component method may also be used as detection logic.

Another preferred embodiment (B) provides a handheld device suitable for use with a drop of blood and uses disposable transducers. Like embodiment (A), this embodiment, described below, includes a handheld device and will measure hematocrit, the hemoglobin content, and/or the other red blood cell indices. Unlike embodiment (A), though, embodiment (B) preferably includes disposable transducers, which are preferably integrated into the sample chamber.

The test chamber of this embodiment may be in either format described in Embodiment (A) with the exception that the test chambers in Embodiment (B) preferably include one or two disposable transducers built into the test chamber. This chamber with would then use an electrical connection to the test device instead of acoustic coupling. These disposable transducers may be preferably manufactured using micromachined capacitive elements (MEMS) to minimize cost.

The disposable transducers are preferably in the 10 to 100 MHz range, more preferably 20 MHz. A pair of these transducers is preferably used, one on each side of the collected sample. These disposable transducers may or may not be in contact with the drawn blood sample.

Another preferred embodiment (C), described below, provides a handheld device suitable for use with a tube of blood and using permanent transducers. This embodiment varies from (A) and (B) in that a larger volume of blood is used. In this embodiment, the user draws a tube of blood from the patient via venipuncture. The sample is placed into the device and the device displays the hematocrit, the hemoglobin content, and/or the mean cell volume. The device is preferably handheld, battery powered, and portable. The sample chamber is preferably disposable.

The test chamber may be a medical tube configured for the introduction of reagents. The tube is inserted into the invention and the transducers couple directly to its outside surface. Two modes of signal propagation are preferable. In the first, the signals are transmitted perpendicularly to the tube axis and transmit through the tube for pitch-catch measurements and reflect off the walls for pulse-echo measurements as shown in FIG. 8. In the second mode, the signal travels along the axis of the tube or perpendicularly but reflect from a disposable, two-step reflector of known size that has previously been inserted into the tube as shown in FIG. 6.

In another preferred embodiment, the measurement is made in-vivo, without drawing any blood from the patient. The device is held against the patient's skin and sends ultrasound into the patient. The backscatter, speed of sound, attenuation, and other ultrasonic measurements are calculated from the received signals and used to infer the blood properties. An array transducer is preferable so that the device can dynamically steer the sound beam and alter the focus length to search for a large artery or vein. If an array transducer is chosen, an appropriate signal generator to control the array and allow the beam-steering is preferred.

III. Use of HCT for Improved Hemostasis Characterization

In another embodiment, the HCT and associated parameters are used in conjunction with conventional measures of hemostasis, as output by sonorheometry. Variations of HCT level, such as in the case of hemodilution, affect the results of conventional coagulation tests such as the PT, PTT and ACT.

Figure 18:
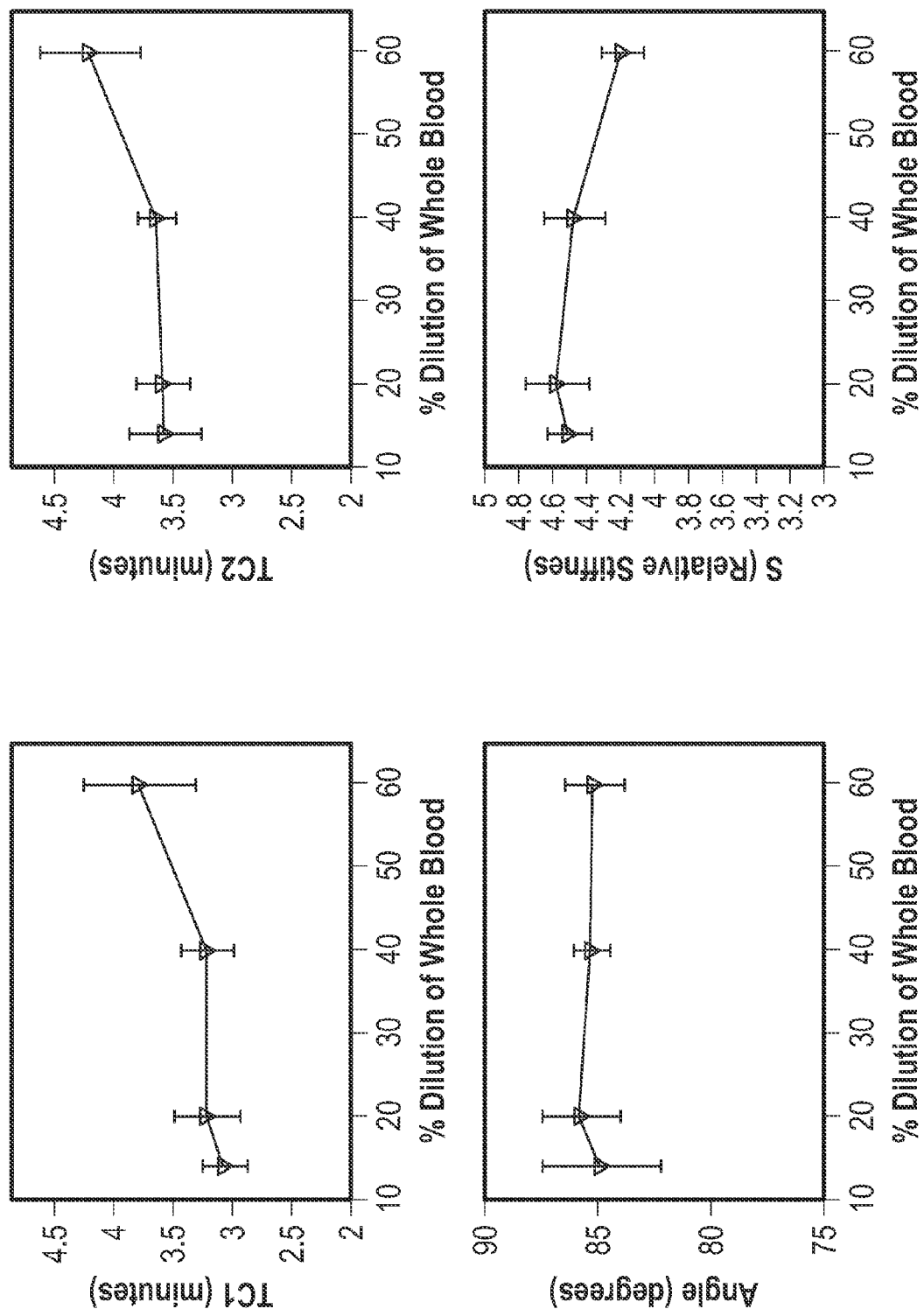
FIG. 18 is a plot of the effect of hemodilution on sonorheometry parameters.

FIG. 18 shows how sonorheometry parameters TC1, TC2, angle, and estimated stiffness S vary as a function of hemodilution, which causes the HCT to change. The data shown in this figure was obtained from whole blood samples from 5 healthy individuals. Increasing amounts of normal saline were added to the whole blood samples to reduce the HCT. Since sonorheometry uses ultrasound signals to perform measurements of hemostasis and the same ultrasound signals can be used to estimated HCT, the parameters output by sonorheometry can be corrected to adjust for the HCT effects shown in FIG. 18.

In another embodiment, sonorheometry can be further modified to output and display HCT level in addition to the hemostatic indexes presented in Table II. Transfusion protocols often use the HCT value as a trigger to transfuse packed red blood cells (RBCs) units. Therefore, in a single device sonorheometry can output a index for (1) coagulation factors (intrinsic and/or extrinsic), (2) platelet function, (3) fibrinogen, (4) fibrinolysis, and (5) HCT so that it can provide guidance for the transfusion of: (1) fresh frozen plasma, (2) platelet concentrates, (3) cryoprecipitate, (4) antifibrinolytics, and (5) packed RBCs, respectively.

In a further embodiment, HCT measurements can be used to improve or correct coagulation parameters to be closer to those obtained for plasma measurements such as described by Amukele T K et al. *Comparison of Plasma With Whole Blood Prothrombin Time and Fibrinogen on the Same Instrument*. American Journal of Pathology 2010. For example, the prothrombin time (PT), international normalized ratio (INR) and fibrinogen viscoelastic assays can vary due to the impact of HCT when in certain ranges.

In one embodiment, the present invention accounts for the impact of HCT by comparing the HCT to an assumed value (if any) or by determining a range in a clotting parameter in which the measured parameter is particularly sensitive to HCT and communicating this to the healthcare personnel.

Also, the present system or process can use empirically determined relationships characterizing the variation of hemostasis parameters with changes in HCT and other oxygen transport parameters to correct or adjust the estimated hemostasis parameter. For example, the system could apply linear regression to empirical data to determine a corrected hemostasis parameter. Also, the system could use a higher order curve, such as a parabola, to determine a corrected hemostasis parameter.

Physiological adjustments as defined herein use the relationships within living or biological systems to correct or adjust measurements. For example, the above-described use of a known physiological relationship between HCT and hemostatic parameters is a physiological adjustment.

Physical adjustments as defined herein use pure physical principals independent of living systems to correct or adjust measurements. For example, the use of speed of sound to calibrate the applied radiation force is a physical adjustment.

IV. Integrated System for Determination of Hemostasis and Oxygen Transport Parameters Integration of the determination of oxygen transport parameters and hemostasis parameters is facilitated by several improvements over the prior art. The term "integrated" as used herein refers to a system or process that uses common or shared hardware or a common sample. Also, data from the same transmission could be used as a form of integration.

Thus, the system may determine hemostatic and oxygen transport parameters using the same blood sample and/or the same transducer or transducers, or at least common hardware and/or sample portions. Integration therefore reduces the time, cost and complexity of determining these important clinical hemostatic and oxygen transport parameters.

The system or device achieves this by being able to operate in two modes without entirely or at all changing the sensor or sample configuration. Prior art systems, on the other hand, for example may use a twisting weight supported by a wire to determine clot stiffness. Such systems are incapable of transmitting or measuring sound through a blood sample. Conversely, prior art systems for measuring the speed of sound through blood are incapable of determining hemostatic parameters. They cannot, for example, induce displacements of clots or measure the induced displacement.

Figure 26:
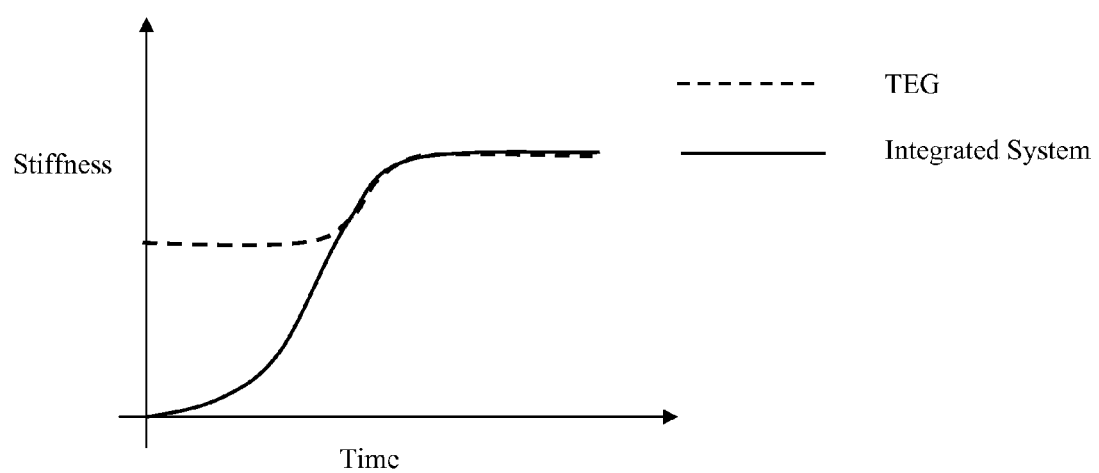
FIG. 26 is a plot comparing a prior art TEG system's sensitivity to the present system.

Also, prior art systems do not have the capabilities of the present system or device to determine hemostatic parameters. The present system or device may also have the ability to dynamically adapt to the properties of the sample through a large stiffness range. FIG. 26 schematically illustrates the impact of the improved dynamic range on clot stiffness measurements compared to a conventional device.

Another advantage is that the system may also be configured to adapt to or adjust to the characteristics of the clot. The adaptation capability can apply a "light touch" to the clot by changing the emitted sound signal to adjust to the properties of the clot. This avoids tearing of the clot. The prior art pendulum systems are relatively insensitive to softer clots and/or can tear or damage a clot during testing, distorting the measurements.

In addition, the ability of the integrated system to adapt reduces electronic noise for greater sensitivity to small echoes. The present system or device has a relatively high sensitivity throughout the large stiffness range.

Also, the system is capable of an increased rate of pulses, resulting in greater forces, further expanding the dynamic range. The pulse frequency range may, for example, be from 1 Hz to 50 kHz. Overall, the system or device may be capable of measuring tissue stiffness in a range of five or more ($10^5$ or greater from softest to hardest) orders of magnitude.

Another advantage of the system or device is its low number of moving parts compared to prior art mechanical systems that employ weights or cantilevers. These attributes offer another advantage by facilitating miniaturization of the system or device. Also, because the sensing system requires no moving parts, the sensing system performs better when subjected to environment vibrations.

Figure 19:
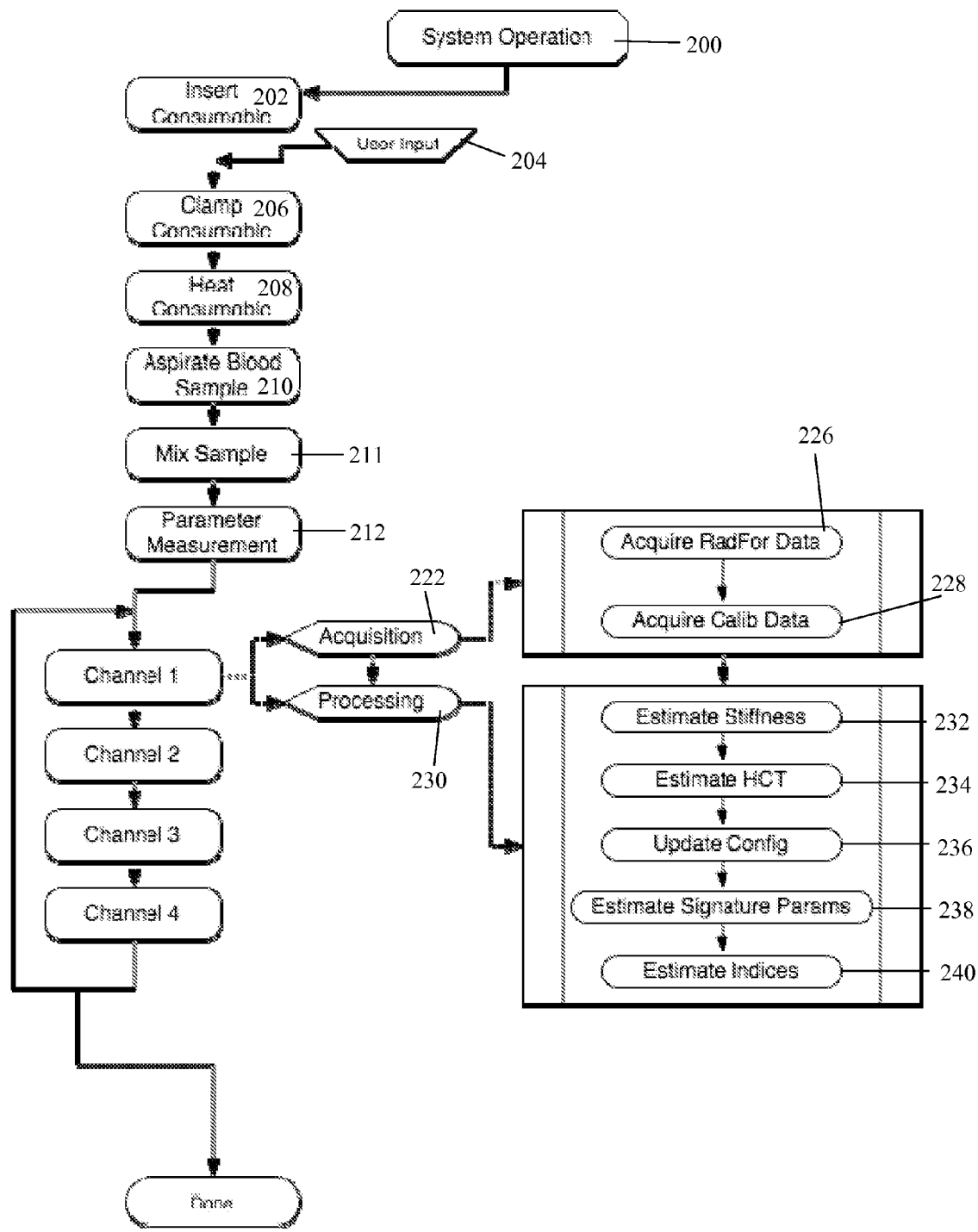
FIG. 19 is a flowchart of an integrated system for determining hemostasis and HCT parameters.

An exemplary process or system 200 for integrated determination of one or more hemostasis parameters and one or more oxygen transport parameters is shown in FIG. 19. A consumable cartridge or other container 30 is inserted 202 by the user into the hemostasis system assembly 1. A syringe containing a blood sample 51 is then manually attached to the consumable.

User input is provided 204 to the hemostasis system assembly 1. For example, the user may confirm that the consumable 30 is in place by pressing a "start" button. Other input may be provided that facilitates or improves determining of the parameters. For example, the input may include identification of the patient associated with the sample.

The device 1 clamps 206 the consumable by applying pressure to the consumable. This pressure may form an acoustic coupling between the consumable and an acoustic wave generating transducer or device 10. The consumable 30 may include aspects of the acoustic wave generating device 10, such as consumable lenses.

The consumable 30 is heated 208 to a temperature that facilitates blood coagulation. A two-way pumping mechanism of the assembly 1 draws or aspirates 210 blood from the sample 51 into the consumable 30.

The blood sample 51 is acoustically mixed 211 with a reagent in a well of the consumable.

Parameters are measured 212 by repeatedly cycling through data acquisition processes in each transducer channel (e.g., 4 transducer channels) while blood coagulates in the consumable 30.

Data is acquired 222 and processed 224 from each channel of the transducer 10. Each channel may have dedicated acquisition 222 and processing 224 before the system 1 moves on to the next channel.

Acquisition 222 may include two steps, radiation force (RadFor) data acquisition 226 and calibration data acquisition 228.

Figure 20:
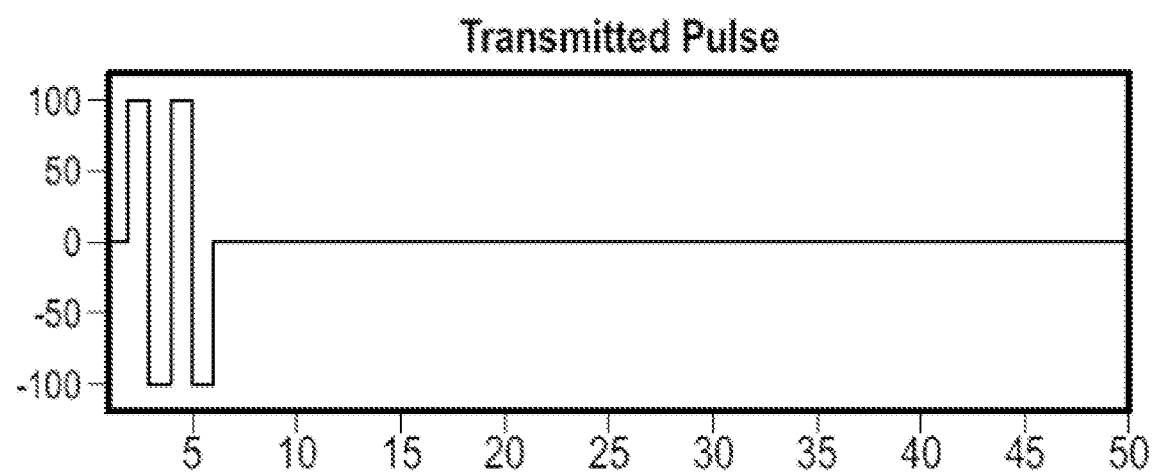
FIGS. 20 and 21 are a short ultrasonic pulse with a correlation function such as may be used in the system of FIG. 19.

As shown in FIG. 20, radiation force data acquisition 226 includes transmission of an ensemble of relatively high intensity acoustic pulses into the blood sample. The system 1 then receives acoustic echo data back from each individual pulse or from a selected subset of the transmitted pulses. Each ensemble of acoustic pulses may be adaptively controlled.

Calibration data acquisition 228 includes transmission of a single acoustic pulse that targets the back of the consumable 30. From this pulse the system 1 derives values for the speed of sound in the blood sample and the acoustic attenuation. More details about radiation force data acquisition 226 and calibration data acquisition 228 are described below.

Acquired data is processed 230 by application of several sub-processes, including estimating stiffness 232, estimating HCT (or other oxygen transport parameter) 234, updating the configuration 236, estimating signature parameters 238 and estimating indices 240.

Estimating stiffness 232 includes accepting raw data acquired from the radiation force acquisition 226 and processing it to yield a single stiffness estimate based on the transmitted radiation force ensemble parameters and the calibration parameters.

Estimating HCT 234 includes deriving a speed of sound and acoustic attenuation from the calibration data acquisition 228 by applying a mathematical model. For example, the estimation sub-process could use a linear mathematical model correlating the speed of sound to hematocrit.

Update the configuration 236 is part of the adaptive acoustic system and includes accepting the maximum displacements acquired during radiation force acquisition 226 and the transmitted ensemble configuration to determine the configuration that will be used for the next ensemble of pulses. The adaptive process is described in more detail below.

Estimating signature parameters 238 includes accepting the single stiffness value from the estimating stiffness 232 sub-process into a matrix containing all of the measured stiffness values for that channel. This sub-process combines all of the stiffness data acquired thus far and fits a non-linear curve to the data. The signature parameters are determined from the non-linear curve. The signature parameters, for example, are the baseline stiffness, time to clot, rate of clot formation, time to lyse, post-lysis stiffness.

Estimating indices 240 includes computing hemostatic indices based on the signature parameters.

The acquisition 222 and processing 224 steps are cycled continuously for each of the four channels until the blood coagulation process is complete.

In a more detailed description of the radiation force acquisition process, each of a plurality of channels is configured to transmit Tx and receive Rx sonic energy to determine a point on a time displacement curve. The four channels generate four transmissions Tx0, Tx1, Tx2, Tx3 and receive four signals Rx0, Rx1, Rx2, Rx3.

Figure 24:
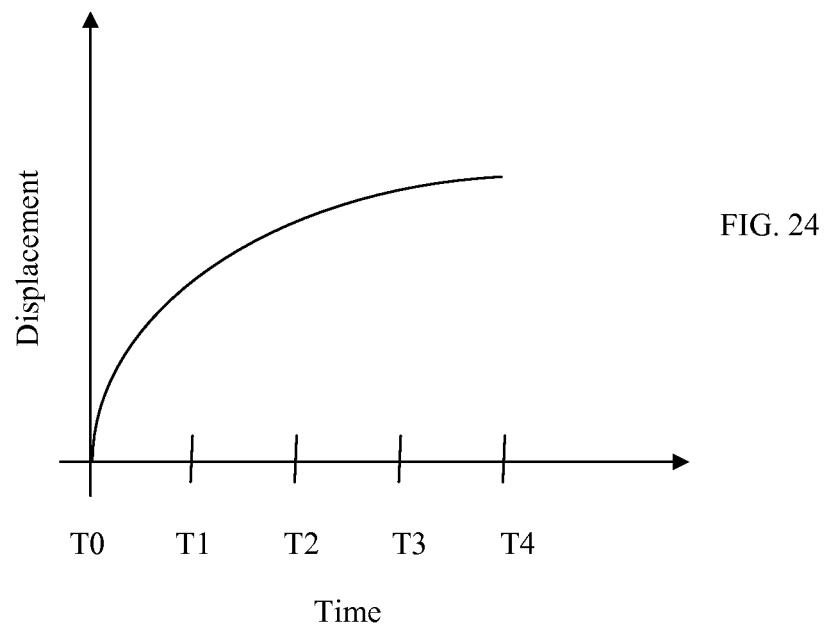
FIG. 24 is a plot of displacement over time of a clot measured by the system of FIG. 19.

The acquired data is then filtered to determine a time-displacement curve at four equal periods, a shown in FIG. 24. Filtration, for example, may be by a principal components filter, such as is described in U.S. Patent Application Publication No. 2009/0304246 to Walker et al. entitled REDUCTION OF ECHO DECORRELATION FACILITATING MOTION ESTIMATION which is incorporated by reference herein in its entirety.

The filtered points are then curve fit using a model, such as a viscoelastic model described above, to estimate a displacement at a time of interest. For example, displacements could be determined at a one second time interval.

Figure 9:
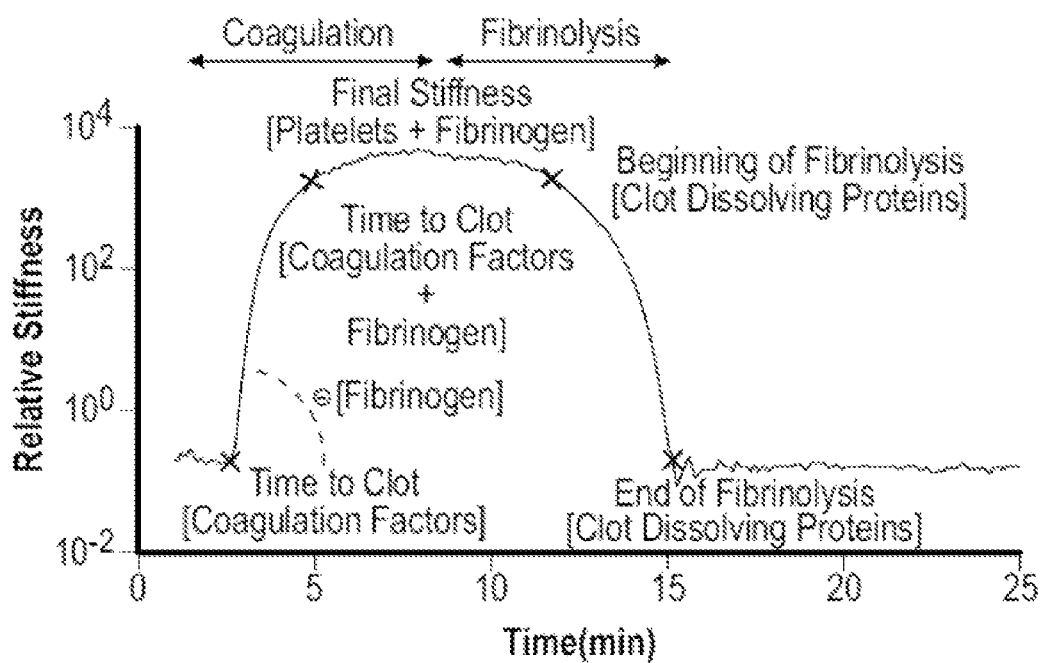
FIG. 9 is a plot of a curve showing evolving clot stiffness over time during hemostasis.

These curves are then used to determine a stiffness value throughout the hemostasis cycle, as shown for example by FIG. 9. Stiffness could be calculated at various intervals depending upon available or desired use of computational power. For example, a 6 second interval yields fairly robust curves while conserving processing power.

Since the amount of force applied is a function of pulse repetition frequency (PRF), the applied force can be adjusted by changing the PRF. The sensitivity could also be adjusted by changing the time at which the displacement is projected, such as to ½ second from 1 second.

Figure 27:
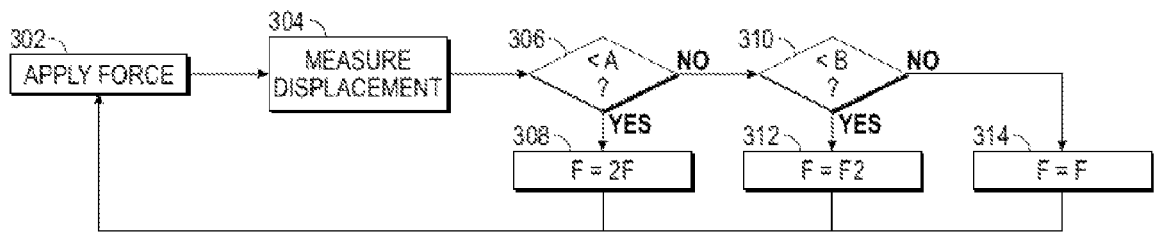
FIGS. 27 and 28 are flowcharts of application of adaptive force to a tissue sample.
Figure 28:
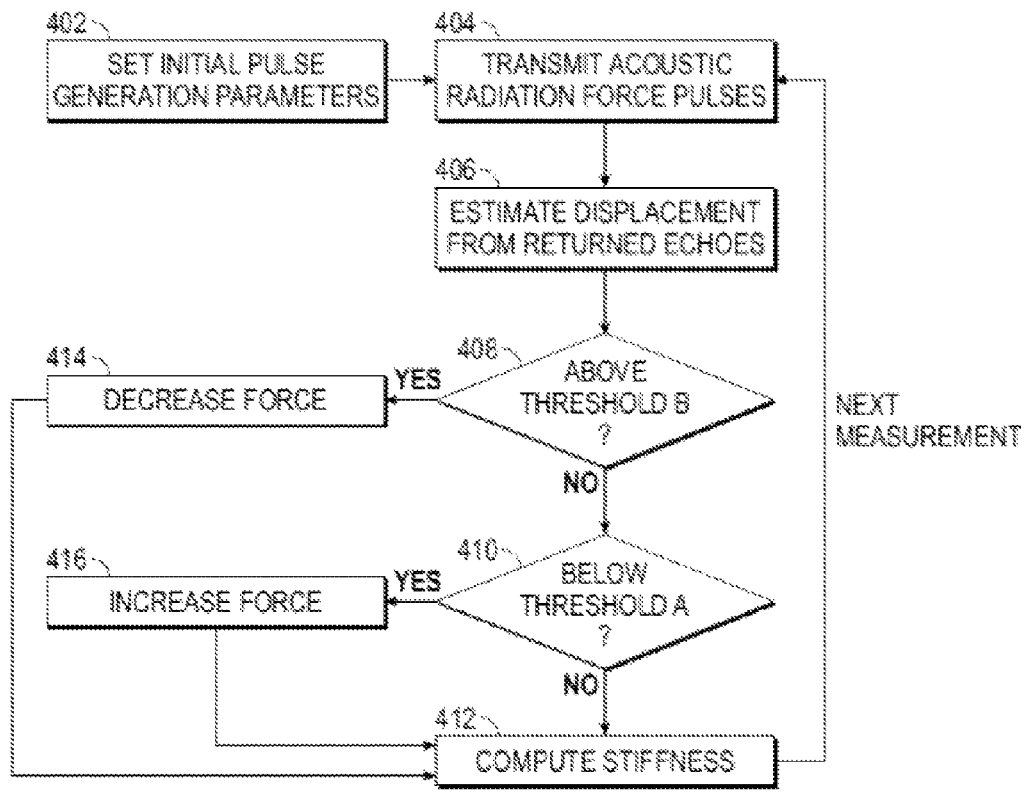

Dynamic adaptability of the present system or device is shown in PCT Patent Application Publication No. WO 2011/035162 to Walker et al. entitled ULTRASOUND-BASED METHOD AND RELATED SYSTEM TO EVALUATE HEMOSTATIC FUNCTION OF WHOLE BLOOD which is incorporated by reference herein in its entirety. FIGS. 27 and 28 show a principle and process of applying adaptive force to a sample for high dynamic range measurement performed at low strain levels according to an embodiment of the present invention.

FIG. 27 is a flow chart illustrating an example of the principle of applying adaptive force to a sample for high dynamic range measurement performed at low strain levels according to an embodiment of the present invention. In this embodiment, a minimum displacement threshold level "a" and a maximum displacement threshold level "b" are preset prior to application of force. At event 302, force F is applied to the target being measured according to an embodiment of the present invention. At event 304 a displacement of the target that resulted from application of the force F to the target in event 302 is measured. At event 306, the measured displacement is compared to the minimum displacement threshold level "a".

If the measured displacement is less than "a", then the force F is increased at event 308 (e.g., doubled, in the embodiment shown in FIG. 2) and this greater force is then applied at event 302 to take the next measurement at event 304.

If, on the other hand, the measured displacement not less than "a", then a comparison is made at event 310 as to whether the measured displacement is greater than maximum displacement threshold level "b".

If the measured displacement is greater than "b", then the force is reduced at event 312 (e.g., halved, in the embodiment shown in FIG. 2) and this lesser force is then applied at event 302 to take the next measurement at event 304. If, on the other hand, the measured displacement not greater than "b", then the force is maintained at its current level at event 314 and the same force is applied at event 302 for taking the next measurement.

In the system or device, an increase of the force F may be accomplished by increasing the PRF. Conversely, a decrease of the force F may be achieved by decreasing the PRF.

Using the principle described with regard to FIG. 27, the present invention can carry out sonorheometry at low strains with a dynamic range of stiffness measurements of approximately five orders of magnitude. Of course, the present invention is not limited to increasing by doubling or decreasing by half, as any arbitrary multipliers can be implemented to carry out the described principle. Possibilities include greater than one for increasing, and less than one, but greater than zero, for decreasing. Likewise, as noted above, increasing and decreasing functions need not be limited to changing the PRF. They can alternatively be carried out by changing the pulse intensity integral (PII) or by changing both PRF and PII.

FIG. 28 is a flow chart illustrating use of adaptive radiation force sonorheometry to adaptively adjust the applied radiation force in order to maintain low strains and improve dynamic ranges (thereby increasing the signal to noise ratio) of stiffness measurement according to an embodiment of the present invention. At event 402, initial parameters are set for PRF and PII, thus defining the initial pulse generation parameters.

The initial PRF is set at a value with the range of from about 4 Hz to about 12 kHz, or less than or equal to 100 Hz, although the present invention is not limited to these settings. Pulses with as little as one cycle up to pulses with sixteen or more cycles can be used. Amplitude may be varied such as increasing (up to doubling, or more) or decreasing (down to halving, or less). In cases where an emission transducer of relatively low efficiency is used, PRF and PII may be set relatively higher. For applications to plasma, which has a lower viscosity than whole blood, relatively lower PII and PRF may be set. Also, when examining plasma, it may be necessary to add an acoustic scattering agent, such as polystyrene microspheres.

At event 404, acoustic radiation force pulses are transmitted to the target according to the PRF and PII that were initially set in event 402. At event 406 a displacement of the target is estimated or measured by sonorheometry, using echoes returned from the target. At event 408, the estimated displacement value is compared with the maximum displacement threshold value "b". If the estimated displacement value is greater than "b", then the force to be applied to the target in the next iteration is set to be decreased by decreasing the PRF and/or decreasing the PII at event 414 and a relative stiffness value (or absolute stiffness value in embodiments where the constants a and c are measured) is computed at event 412, using the estimated displacement value. Next, event 404 is carried out again by transmitting decreased force generated using the parameters from event 414.

If, on the other hand, the estimated or measured displacement value is not greater than "b" at event 408, then at event 410 the estimated displacement value is compared with the minimum displacement threshold value "a". If the estimated displacement value is less than "a", then the force to be applied to the target in the next iteration is set to be increased by increasing the PRF and/or increasing the PII at event 416 and a relative stiffness value (or absolute stiffness value in embodiments where the constants a and c are measured) is computed at event 412, using the estimated displacement value. Next, event 404 is carried out again by transmitting increased force generated using the parameters from event 414. Iterations can be carried out until all physiological observations that the observer is interested in have been made, e.g., until an experiment is ended, until a patient is released to another care center, until a clot completely dissolves, etc.

As another option, the systems of FIGS. 27 and 28 may include a curve comparison step in place of, or in addition to, or as part of, steps 306, 310, 408 or 410. This curve displacement step compares the measured time-displacement curve to an expected model curve. The fit of the measured curve to the expected model curve is quantified. If it is below the threshold the force is reduced. Without being wed to theory, the assumption is that the poor fit is because large displacements are causing signal decorrelation.

Sensitivity is related to the amount of force applied to the sample, which results in higher displacements.

Advantageously, as shown above, short pulses also do not smear as much due to the lack of overlap in the return signal. However, the overall amplitude of the response may be somewhat small. The return signal amplitude could be increased through an increase in the amplitude of the transmitted pulse. However, power limitations can curtail the size of the amplitude, especially in systems where the peak-to-peak power potential is limited to 200V because of the electronic components used. Longer pulses may result in a stronger "push" also, but can result in smear due to overlap in the return signal.

However, further advantageously, the present system and device may include processes for ameliorating the smear effects. For example, coded excitation could be used to improve force measurement and imaging.

Radiation force based sensing is limited by the available signal to noise. For sonorheometry, the fundamental signal is radiation force induced displacement. The noise is the error in estimation of that displacement. The signal (displacement) is determined, at a given material stiffness, by the applied radiation force:

$$F = W/c$$

Wherein W is the acoustic power and c is the speed of sound. Increasing force yields increasing displacement, improving the accuracy of the displacement estimates. While the speed of sound, like stiffness, is largely an intrinsic property, the applied acoustic power can be controlled by the system.

The applied acoustic power emitted by a pulsed system is a function of the pulse repetition frequency (PRF) and the acoustic Pulse Intensity Integral per pulse:

$$W = PRF * PII$$

The PRF can be greatly increased to increase force applied to the sample. Power increases, however, may be limited. Application of a high PRF may cause echoes from earlier pulses to overlap in time with the desired echoes from the most recently transmitted pulse. This makes it difficult to cleanly estimate displacement. Further, if the PRF is too high then it becomes challenging to transfer the digitized echo data from one transmission before echo data is digitized from the following transmission. For these reasons it is desirable to increase the power per transmitted pulse (Pulse Intensity Integral).

The PII in each transmitted pulse is proportional to the integral of the square of the acoustic pressure in that pulse. A first strategy is to increase the amplitude of the acoustic pulse. This can be accomplished by increasing the drive voltage of the transmit circuit. However, the circuitry of the emitter is usually limited to +/−100V to avoid damage.

The length of the emitted pulse could also be increased. One would maintain the same center frequency but increase the number of cycles in the transmission. This approach however will reduce the signal bandwidth and the axial resolution of the system. These changes may reduce the available window for measuring displacement by overlapping the desired region with signals from the undesired region. Further, the accuracy of displacement estimates is reduced as described by the Cramér-Rao Lower Bound.

The radiation force sensing could be improved if pulse length could be increased without degrading the axial resolution or bandwidth, such as by using coded excitation. For example, Barker Codes could be used. Barker codes are simple binary codes that have the property of having very short correlation lengths when convolved with the proper matched code. These codes preserve bandwidth and spatial resolution while still lengthening the transmitted pulse.

Figure 21:
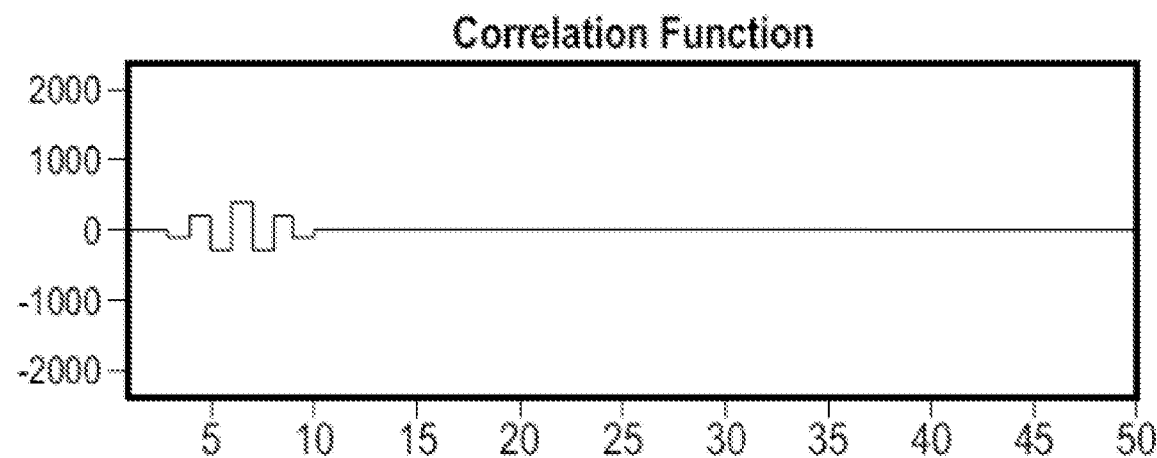

For example, a two-cycle transmit pulse is shown in FIG. 20. The associated correlation function shown in FIG. 21 is quite short, indicating that good spatial resolution in maintained. It is also quite low in amplitude however, indicating fairly low transmit energy.

Figure 22:
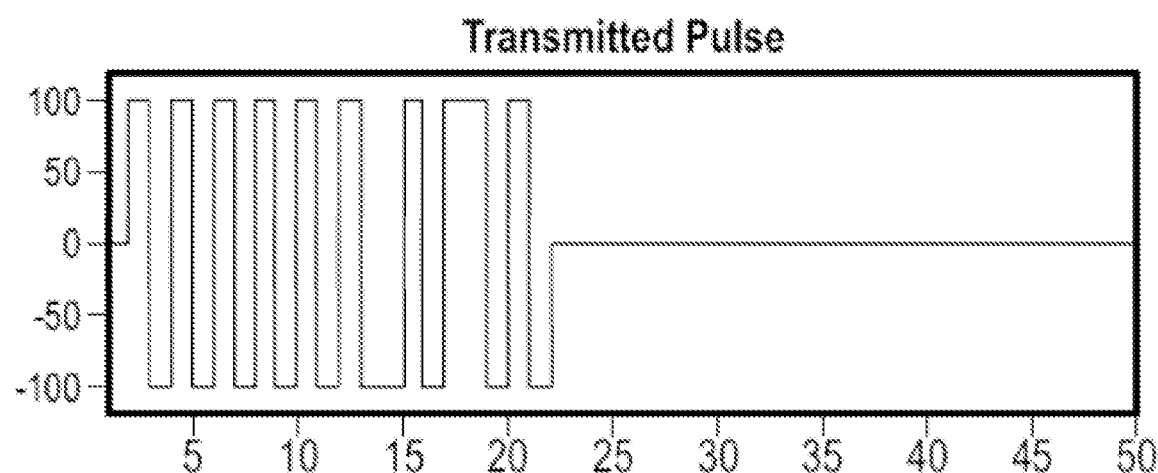
FIGS. 22 and 23 are a longer ultrasonic pulse with a correlation function such as may be used in the system of FIG. 19.
Figure 23:
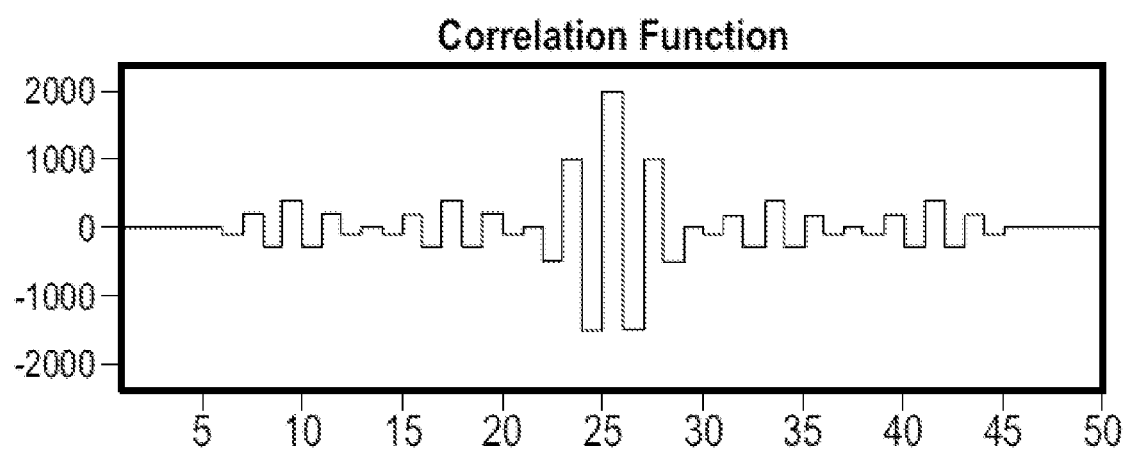

As shown in FIG. 22, the original two cycle transmit pulse is replaced by a version of that pulse convolved with a 5 sample Barker code (+++−+). The transmitted pulse is now five times longer, generating a significantly higher (5×) peak in the autocorrelation function. The transmission is much more energetic. The correlation function itself however remains quite short in duration, as shown in FIG. 23, indicating that axial resolution is largely preserved. Modest ringing is introduced, but this is a reasonable tradeoff for the large increase in displacement that will be achieved.

As can be seen above by the adaptive process, improving dynamic range may be a matter of incrementally improving the electronic signal-to-noise, increasing the applied force at one end (high stiffness) and reducing the applied force at the other end (low stiffness). At the low end may be a 2 cycle transmission at 4 Hz PRF. At the high end, a 13 point barker code with 2 cycle impulse response for a 26 cycle transmit at 32 KHz PRF may be employed. The high to low force variation is by a factor of 212,992.

Prospectively, the inventors believe a system could be built with two transmit waveforms voltages could be employed, such as +/−100 V and +/−25 V. Since the force depends upon the square of the voltage, the range would increase by a factor of 8 to 1,703,936.

Also, the inventors have observed the impact of the range of sensitivity to motion. At the high end, displacements as small as 0.1 micron may be estimated. At the low end, displacements may be as high as 75 microns (half a wavelength). This yields a 750× displacement range. Spline-based algorithm displacement estimators may yield a 750 micron measurement. A conservative motion estimation is therefore 1,277,952,000 and even as high as 12,779,520,000.

Thus the dynamic range with "simple" signal processing is just over 9 orders of magnitude. With more sophisticated signal processing just over 10 orders of magnitude may be achieved.

Thus, even 5 orders of magnitude can be exceeded in the present system or device through various improvements. First, the use of two different transmit levels gives us almost one order of magnitude. Second, using barker codes gives us more than one order of magnitude. Also, a broad range of transmit pulse repetition frequencies is being used. Also displacement estimation noise is kept at a low baseline which, although not easy, is achievable. Generally, 5 orders of magnitude is enough to capture the stiffness range of blood in most instances.

The present system or device can also improve sensitivity through the use of multiple samples. For example, four wells with different reagents could be used to determine measurements within overlapping time periods.

Figure 25:
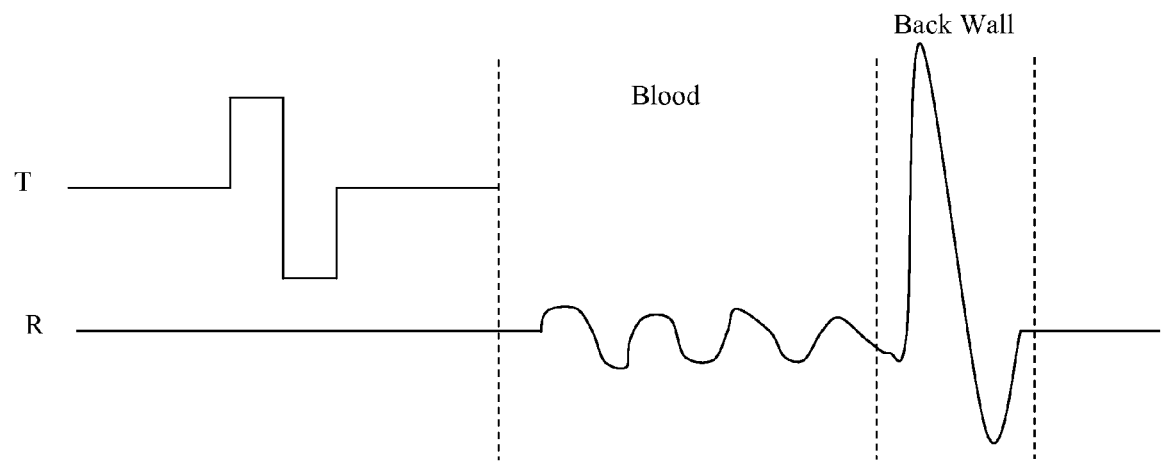
FIG. 25 is a plot of a short pulse and response during calibration of the system of FIG. 19.

Use of the calibration acquisition process facilitates collection of oxygen transport parameters such as HCT. As shown in FIG. 25, shorter pulses are generated during calibration resulting in a delayed response compared to the echoes returned by the blood. This may be due to the further distance of the back wall of the sample container, for example. The system or device is configured to measure, including amplitude and time, from both the blood and the back wall of the container. HCT can be determined using a linear model wherein:

$$HCT = \alpha + \beta_{AMP} + \gamma_{TIME}$$

Alpha ($\alpha$) is a fixed constant. Beta ($\beta_{AMP}$) is related to the amplitude and gamma ($\gamma_{TIME}$) is related to the time duration of the return signal based on its arrival time.

Figure 29:
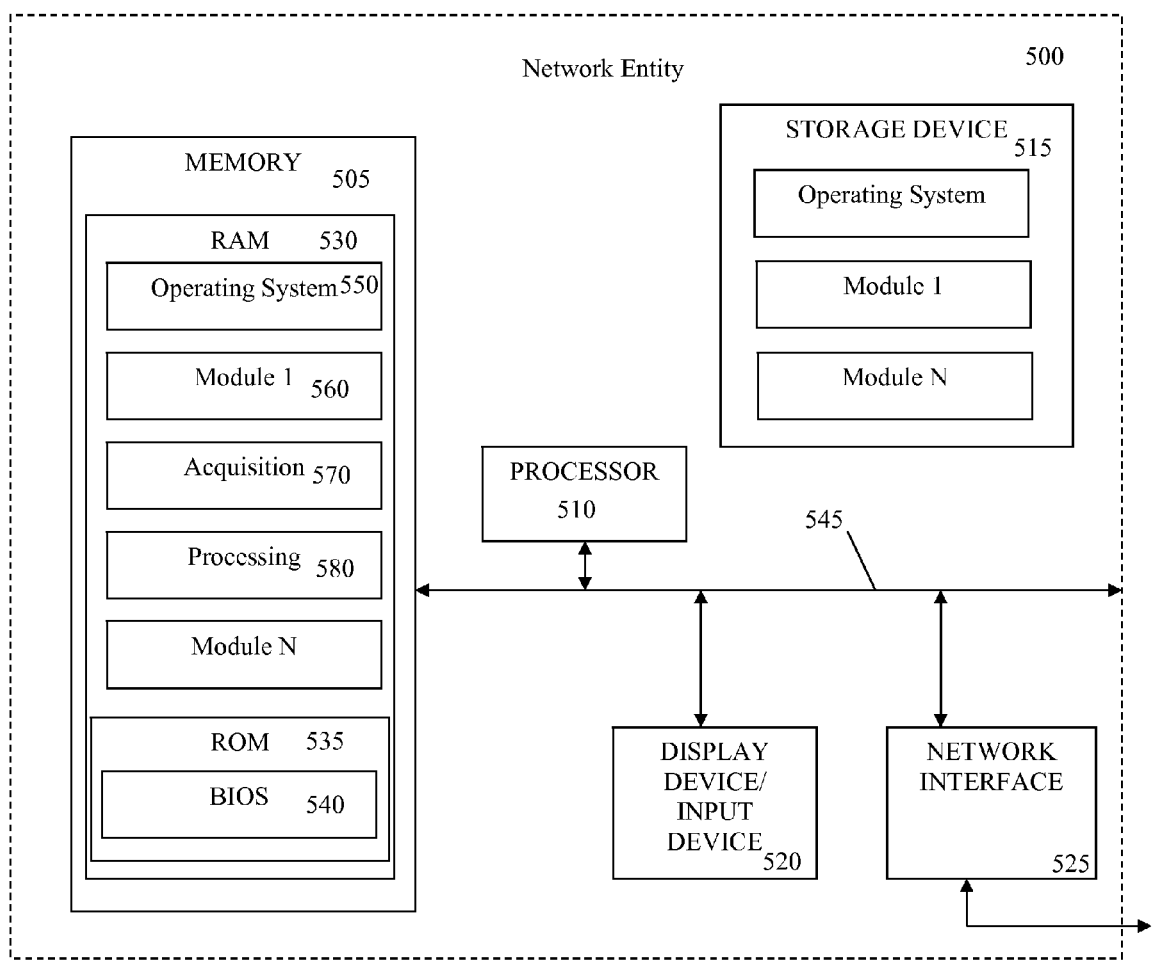
FIG. 29 is a network entity for characterizing soft tissue parameters.

Referring now to FIG. 29, a schematic diagram of a central server 500, or similar network entity, configured to implement a system or process disclosed herein is provided. As used herein, the designation "central" merely serves to describe the common functionality the server provides for multiple clients or other computing devices and does not require or infer any centralized positioning of the server relative to other computing devices.

As may be understood from FIG. 29, in this embodiment, the central server 500 may include a processor 510 that communicates with other elements within the central server 500 via a system interface or bus 545. Also included in the central server 500 may be a display device/input device 520 for receiving and displaying data. This display device/input device 520 may be, for example, a keyboard or pointing device that is used in combination with a monitor. The central server 500 may further include memory 505, which may include both read only memory (ROM) 535 and random access memory (RAM) 530. The server's ROM 535 may be used to store a basic input/output system 540 (BIOS), containing the basic routines that help to transfer information across the one or more networks.

In addition, the central server 500 may include at least one storage device 515, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 515 may be connected to the system bus 545 by an appropriate interface. The storage devices 515 and their associated computer-readable media may provide nonvolatile storage for a central server. It is important to note that the computer-readable media described above could be replaced by any other type of computer-readable media known in the art. Such media include, for example, magnetic cassettes, flash memory cards and digital video disks.

A number of program modules may be stored by the various storage devices and within RAM 530. Such program modules may include an operating system 550 and a plurality of one or more (N) modules 560. The modules 560 may control certain aspects of the operation of the central server 500, with the assistance of the processor 510 and the operating system 550. For example, the modules may perform the functions described above and illustrated by the figures, such as FIGS. 19, 27 and 18, and other materials disclosed herein. The modules may include, for example, an acquisition module 570 and a processing module 580 for performing the operations described in reference to FIG. 19.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

That which is claimed:

1. A system for determining properties of at least one blood sample, the system comprising:
   a receiver that detects a response resulting from an application of a signal to the blood sample and generates data quantifying the response to the applied signal; and
   a processor and a memory in communication with the processor, the memory having computer-executable instructions comprising the steps of:
      receiving, at the processor, the data quantifying the response to the applied signal, and
      determining at least one hemostasis parameter and at least one oxygen transport parameter of the blood sample using at least a portion of the data, wherein determining at least one hemostasis parameter and at least one oxygen transport parameter further comprises adjusting the hemostasis parameter using the oxygen transport parameter.

2. A system of claim 1, wherein at least some of the data is generated by an application of force to the blood sample.

3. A system of claim 2, wherein the blood sample comprises a common sample portion and wherein the hemostasis parameter and the oxygen transport parameter characterize the common sample portion.

4. A system of claim 3, further comprising at least one sample container that contains the common sample portion.

5. A system of claim 3, wherein the common sample portion is an in-vivo blood sample.

6. A system of claim 2, wherein the receiver detects the response by determining a displacement of the blood sample.

7. A system of claim 6, wherein the application of a signal to the blood sample comprises an ultrasonic signal generated and directed at the blood sample to induce the displacement.

8. A system of claim 7, wherein determining at least one hemostasis parameter and at least one oxygen transport parameter further comprises determining a stiffness of the blood sample using the data quantifying the response.

9. A system of claim 8, wherein the data quantifying the response includes a backscatter of the ultrasonic signal applied to the blood sample, and wherein determining at least one hemostasis parameter and at least one oxygen transport parameter further comprises using the backscatter of the ultrasonic signal to determine the oxygen transport parameter.

10. A system of Claim 1, wherein determining at least one hemostasis parameter and at least one oxygen transport parameter further comprises determining the oxygen transport parameter and the hemostasis parameter from a common portion of the data.

11. A system of claim 1, wherein the oxygen transport parameter is at least one parameter selected from a group consisting of HCT, HGB, MCV, RBC, MCHC, MCH and combinations thereof 12. A system of claim 1, further comprising a graphical user interface that displays the hemostasis parameter and the oxygen parameter simultaneously.

13. A system of claim 1, wherein the application of a signal to the blood sample comprises generating an ultrasonic signal and directing the ultrasonic signal to the blood sample, and wherein the receiver detects at least one characteristic of the ultrasonic signal resulting from the application of the ultrasonic signal to the blood sample.

14. A system of claim 13, wherein the computer-executable instructions comprise the step of determining using the at least one characteristic of the ultrasonic signal, the hemostasis parameter and at least one parameter selected from a group consisting of HCT, HGB, MCV, RBC, MCHC, MCH and combinations thereof 15. A system, comprising:
   a memory; and
   a processor in communication with the memory;
   an acquisition module comprising computer-executable instructions, wherein said instructions comprise the steps of:
      applying a signal to a blood sample,
      measuring a response resulting from the applied signal, and
      creating data quantifying the response; and
   a processing module comprising computer-executable instructions, wherein said instructions comprise the steps of:
      receiving the data quantifying the response from the acquisition module; and
      determining at least one hemostasis parameter and at least one oxygen transport parameter of the blood sample using at least a portion of the data, wherein determining at least one hemostasis parameter and at least one oxygen transport parameter further comprises adjusting the hemostasis parameter using the oxygen transport parameter.

16. A system for determining properties of at least one blood sample, the system comprising:
   a displacement means for causing a displacement within the blood sample;
   a measurement means for measuring the displacement within the blood sample;
   a data creation means for creating data characterizing the blood sample;
   a processor means for receiving the data from the data creation means and determining at least one hemostasis parameter and at least one oxygen transport parameter of the blood sample using at least a portion of the data, wherein determining at least one hemostasis parameter and at least one oxygen transport parameter further comprises adjusting the hemostasis parameter using the oxygen transport parameter; and
   an integrated means for facilitating determination of the at least one hemostasis parameter and at least one oxygen transport parameter.

* * * * *